(12) United States Patent
Janssen

(10) Patent No.: US 11,883,361 B2
(45) Date of Patent: Jan. 30, 2024

(54) FLUID TRANSFER DEVICES AND METHODS OF USE

(71) Applicant: ICU Medical, Inc., San Clemente, CA (US)

(72) Inventor: Matthias Janssen, Meinerzhagen (DE)

(73) Assignee: ICU Medical, Inc., San Clemente, CA (US)

( * ) Notice: Subject to any disclaimer, the term of this patent is extended or adjusted under 35 U.S.C. 154(b) by 23 days.

(21) Appl. No.: 17/648,657

(22) Filed: Jan. 21, 2022

(65) Prior Publication Data

US 2022/0142865 A1 May 12, 2022

Related U.S. Application Data

(63) Continuation of application No. PCT/US2021/041891, filed on Jul. 15, 2021.

(60) Provisional application No. 63/054,568, filed on Jul. 21, 2020.

(51) Int. Cl.
*A61J 1/20* (2006.01)
(52) U.S. Cl.
CPC .......... *A61J 1/2003* (2015.05); *A61J 2200/74* (2013.01)
(58) Field of Classification Search
CPC ........ A61J 1/10; A61J 1/14; A61J 1/16; A61J 1/20; A61J 1/22; A61J 1/2003; A61J 2200/74
See application file for complete search history.

(56) References Cited

U.S. PATENT DOCUMENTS

| | | |
|---|---|---|
| 3,768,084 A | 10/1973 | Haynes |
| 3,770,354 A | 11/1973 | Tsuruta et al. |
| 3,778,702 A | 12/1973 | Finger |

(Continued)

FOREIGN PATENT DOCUMENTS

| | | |
|---|---|---|
| AU | 2013216679 | 9/2013 |
| BR | PI0704229-9 | 11/2009 |

(Continued)

OTHER PUBLICATIONS

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.

(Continued)

*Primary Examiner* — Timothy L Maust
(74) *Attorney, Agent, or Firm* — Knobbe, Martens, Olson & Bear, LLP

(57) ABSTRACT

Systems and methods for the transfer of medical fluid are provided. A medical fluid transfer system may comprise a pump configured to transfer fluid through a tube assembly having a first connector configured to couple to a source container and a second connector configured to couple to a target container. The medical fluid transfer system may also comprise a destination sensor configured to output information about the target container. The medical fluid transfer system may further comprise a control system configured to operate the pump based on an operational setting associated with fluid volume; receive measurement data representing a measurement of the target container by the destination sensor, and adjust the operational setting based on an observed volume of fluid transferred to the target container.

19 Claims, 15 Drawing Sheets

(56) References Cited

U.S. PATENT DOCUMENTS

| | | |
|---|---|---|
| 3,806,821 A | 4/1974 | Niemeyer et al. |
| 3,838,565 A | 10/1974 | Carlyle |
| 3,854,038 A | 12/1974 | Mckinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | Kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |

(56) References Cited

U.S. PATENT DOCUMENTS

| | | |
|---|---|---|
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Blomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,769,001 A | 9/1988 | Prince |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,908,019 A | 3/1990 | Urquhart et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,014,798 A | 5/1991 | Glynn |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,040,699 A * | 8/1991 | Gangemi ............. G01G 19/346 141/105 |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |

(56) References Cited

U.S. PATENT DOCUMENTS

| | | |
|---|---|---|
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,749 A | 6/1995 | Merte et al. |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |

(56) References Cited

U.S. PATENT DOCUMENTS

| | | |
|---|---|---|
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,685,866 A | 11/1997 | Lopez |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,734,464 A | 3/1998 | Gibbs |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |

(56) References Cited

U.S. PATENT DOCUMENTS

| | | |
|---|---|---|
| 6,027,441 A | 2/2000 | Cantu |
| 6,028,412 A | 2/2000 | Shine et al. |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,606,047 B1 | 8/2003 | Börjesson et al. |
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |

(56) References Cited

U.S. PATENT DOCUMENTS

| | | | |
|---|---|---|---|
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,171,992 B2 * | 2/2007 | DiGianfilippo ........ G16H 40/63 |
| | | | 141/105 |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Girndt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,343,224 B2 * | 3/2008 | DiGianfilippo ........ G16H 40/63 |
| | | | 700/265 |
| 7,347,836 B2 | 3/2008 | Peterson et al. |
| 7,347,854 B2 | 3/2008 | Shelton et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |

(56) References Cited

U.S. PATENT DOCUMENTS

| | | |
|---|---|---|
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,477,997 B2 | 1/2009 | Kaplit |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,605,730 B2 | 10/2009 | Tomioka et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenskow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,976,508 B2 | 7/2011 | Hoag |
| 7,981,073 B2 | 7/2011 | Mollstam |
| 7,981,082 B2 | 7/2011 | Wang et al. |
| 7,998,134 B2 | 8/2011 | Fangrow |
| 8,002,736 B2 | 8/2011 | Patrick et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,514 B2 | 12/2011 | Butterfield et al. |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blomquist |
| 8,175,668 B1 | 5/2012 | Nabutovsky et al. |
| 8,177,739 B2 | 5/2012 | Cartledge et al. |
| 8,180,440 B2 | 5/2012 | McCombie et al. |
| 8,185,322 B2 | 5/2012 | Schroeder et al. |
| 8,197,444 B1 | 6/2012 | Bazargan et al. |
| 8,219,413 B2 | 7/2012 | Martinez et al. |
| 8,221,395 B2 | 7/2012 | Shelton et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,409,164 B2 | 4/2013 | Fangrow |
| 8,449,524 B2 | 5/2013 | Braig et al. |
| 8,469,942 B2 | 6/2013 | Kow et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,522,832 B2 | 9/2013 | Lopez et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,728,020 B2 | 5/2014 | Caleffi et al. |
| 8,758,306 B2 | 6/2014 | Lopez et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,905,965 B2 | 12/2014 | Mandro et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| 9,190,010 B2 | 11/2015 | Vik et al. |
| 9,240,002 B2 | 1/2016 | Hume et al. |
| 9,272,089 B2 | 3/2016 | Jacobson et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,545,475 B2 | 1/2017 | Borges et al. |
| 9,707,341 B2 | 7/2017 | Dumas, III et al. |
| 9,764,087 B2 | 9/2017 | Peterfreund et al. |
| 9,852,265 B1 | 12/2017 | Treacy et al. |
| 9,883,987 B2 | 2/2018 | Lopez et al. |
| 9,943,269 B2 | 4/2018 | Muhsin et al. |
| 9,995,611 B2 | 6/2018 | Ruchti et al. |
| 10,022,498 B2 | 7/2018 | Ruchti et al. |
| 10,046,112 B2 | 8/2018 | Oruklu et al. |
| 10,089,055 B1 | 10/2018 | Fryman |
| 10,099,009 B1 | 10/2018 | Anderson et al. |
| 10,166,328 B2 | 1/2019 | Oruklu et al. |
| 10,342,917 B2 | 7/2019 | Shubinsky et al. |
| 10,430,761 B2 | 10/2019 | Hume et al. |
| 10,463,788 B2 | 11/2019 | Day |
| 10,549,248 B2 | 2/2020 | Brown et al. |
| 10,578,474 B2 | 3/2020 | Ruchti et al. |
| 10,596,316 B2 | 3/2020 | Dumas, III et al. |
| 10,635,784 B2 | 4/2020 | Rubalcaba, Jr. et al. |
| 10,656,894 B2 | 5/2020 | Fryman |

(56) References Cited

U.S. PATENT DOCUMENTS

| | | |
|---|---|---|
| 10,682,102 B2 | 6/2020 | Declerck |
| 10,709,885 B2 * | 7/2020 | Janders .................. B01F 23/45 |
| 10,850,024 B2 | 12/2020 | Day et al. |
| 10,874,793 B2 | 12/2020 | Oruklu et al. |
| 11,004,035 B2 | 5/2021 | Hume et al. |
| 11,029,911 B2 | 6/2021 | Fryman |
| 11,090,431 B2 | 8/2021 | Dumas, III et al. |
| 11,135,360 B1 | 10/2021 | Jacobson et al. |
| 11,439,570 B2 * | 9/2022 | Lopez .................. E05F 15/643 |
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018289 A1 | 1/2003 | Ng et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0186833 A1 | 10/2003 | Huff et al. |
| 2003/0187338 A1 | 10/2003 | Say et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0216682 A1 | 11/2003 | Junker |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0128162 A1 | 7/2004 | Schlotterbeck et al. |
| 2004/0128163 A1 | 7/2004 | Goodman et al. |
| 2004/0133166 A1 | 7/2004 | Moberg et al. |
| 2004/0145114 A1 | 7/2004 | Ippolito et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0108057 A1 | 5/2005 | Cohen et al. |
| 2005/0119597 A1 | 6/2005 | O'Mahony et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |

(56) References Cited

U.S. PATENT DOCUMENTS

| | | |
|---|---|---|
| 2005/0197621 A1 | 9/2005 | Poulsen et al. |
| 2005/0197649 A1 | 9/2005 | Shelton et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0179436 A1 | 8/2007 | Braig et al. |
| 2007/0191817 A1 | 8/2007 | Martin |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0077116 A1 | 3/2008 | Dailey et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0169044 A1 | 7/2008 | Osborne et al. |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0099866 A1 | 4/2009 | Newman |
| 2009/0105636 A1 | 4/2009 | Hayter et al. |
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |

(56) References Cited

U.S. PATENT DOCUMENTS

| | | |
|---|---|---|
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0312039 A1 | 12/2010 | Quirico et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0137241 A1 | 6/2011 | DelCastilio et al. |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0025995 A1 | 2/2012 | Moberg et al. |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0089411 A1 | 4/2012 | Srnka et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0222774 A1 | 9/2012 | Husnu et al. |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0032634 A1 | 2/2013 | McKirdy |
| 2013/0041342 A1 | 2/2013 | Bernini et al. |
| 2013/0044111 A1 | 2/2013 | VanGilder et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0197930 A1 | 8/2013 | Garibaldi et al. |
| 2013/0201482 A1 | 8/2013 | Munro |
| 2013/0116649 A1 | 9/2013 | Kouyoumjian et al. |
| 2013/0253430 A1 | 9/2013 | Kouyoumjian et al. |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0345658 A1 | 12/2013 | Browne et al. |
| 2013/0345666 A1 | 12/2013 | Panduro et al. |
| 2014/0067425 A1 | 3/2014 | Dudar et al. |
| 2014/0145915 A1 | 5/2014 | Ribble et al. |
| 2014/0180711 A1 | 6/2014 | Kamen et al. |
| 2014/0224829 A1 | 8/2014 | Capone et al. |
| 2014/0267563 A1 | 9/2014 | Baca et al. |
| 2014/0303591 A1 | 10/2014 | Peterfreund et al. |
| 2015/0025453 A1 | 1/2015 | Ledford et al. |
| 2015/0033073 A1 | 1/2015 | Yang et al. |
| 2015/0065988 A1 | 3/2015 | Holderle et al. |
| 2015/0114515 A1* | 4/2015 | Phallen .............. B67C 3/288 |
| | | 141/238 |
| 2015/0168958 A1 | 6/2015 | Downie et al. |

(56) References Cited

U.S. PATENT DOCUMENTS

| | | |
|---|---|---|
| 2015/0265765 A1 | 9/2015 | Yavorsky et al. |
| 2015/0338340 A1 | 11/2015 | Jiang et al. |
| 2015/0343141 A1 | 12/2015 | Lindo et al. |
| 2015/0371004 A1 | 12/2015 | Jones |
| 2016/0042264 A1 | 2/2016 | Borges et al. |
| 2016/0110088 A1 | 4/2016 | Vik et al. |
| 2016/0144101 A1 | 5/2016 | Pananen |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0158437 A1 | 6/2016 | Biasi et al. |
| 2016/0175517 A1 | 6/2016 | Sileika et al. |
| 2016/0193604 A1 | 7/2016 | McFarland et al. |
| 2016/0339167 A1 | 11/2016 | Ledford et al. |
| 2017/0043089 A1 | 2/2017 | Handler |
| 2017/0354941 A1 | 12/2017 | Brown et al. |
| 2018/0018440 A1 | 1/2018 | Sugawara |
| 2019/0091401 A1 | 3/2019 | Ruchti et al. |
| 2019/0262535 A1 | 8/2019 | Shubinsky et al. |
| 2019/0269846 A1 | 9/2019 | Oruklu et al. |
| 2019/0282757 A1 | 9/2019 | Gylland et al. |
| 2020/0069864 A1 | 3/2020 | Shubinsky et al. |
| 2020/0113784 A1* | 4/2020 | Lopez .................. E05F 15/655 |
| 2020/0238007 A1 | 7/2020 | Day |
| 2020/0271499 A1 | 8/2020 | Ruchti et al. |
| 2020/0282137 A1 | 9/2020 | Dumas, III et al. |
| 2020/0324044 A1 | 10/2020 | Gylland et al. |
| 2020/0357500 A1 | 11/2020 | Rubalcaba, Jr. et al. |
| 2021/0170101 A1 | 6/2021 | Cavendish, Jr. et al. |
| 2021/0260283 A1 | 8/2021 | Oruklu et al. |
| 2021/0295263 A1 | 9/2021 | Hume et al. |
| 2021/0397396 A1 | 12/2021 | Fryman |

FOREIGN PATENT DOCUMENTS

| | | |
|---|---|---|
| CA | 2 113 473 | 3/1993 |
| CA | 2 551 817 | 7/2005 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2010-063767 | 3/2010 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/070556 | 8/2004 |
| WO | WO 2004/070994 | 8/2004 |
| WO | WO 2004/112579 | 12/2004 |

(56) References Cited

FOREIGN PATENT DOCUMENTS

| | | |
|---|---|---|
| WO | WO 2005/018716 | 3/2005 |
| WO | WO 2005/030489 | 4/2005 |
| WO | WO 2005/036447 | 4/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/036854 | 3/2013 |
| WO | WO 2013/096769 | 6/2013 |
| WO | WO 2015/134478 | 9/2015 |
| WO | WO 2017/051271 | 3/2017 |
| WO | WO 2017/144366 | 8/2017 |
| WO | WO 2019/092680 | 5/2019 |
| WO | WO 2020/214717 | 10/2020 |

OTHER PUBLICATIONS

Alaris® Medical Systems, "Signature Edition® Gold—Single & Dual Channel Infusion System", San Diego, CA, USA, date unknown, but believed to be at least as early as Nov. 29, 2008, pp. 2-88 & 2-91.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-releases/2014/05_08_14_sigma.page.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Buhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http://www.diffen.com/difference/Continually_vs_Continuously, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
Daimiwal et al., "Wireless Transfusion Supervision and Analysis Using Embedded System", IEEE, 2010 International Conference ICBBT, China, Apr. 2010, pp. 56-60.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
"Decision of the Administrative Council of Oct. 16, 2013 Amending Rule 135 and 164 of the Implementing Regulations to the European Patent Convention (CA/D 17/13)", Official Journal EPO dated Nov. 2013, dated Nov. 2013, pp. 503-506. http://archive.epo.org/epo/pubs/oj013/11_13/11_5033.pdf.
"Decision of the Administrative Council of Oct. 27, 2009 Amending the Implementing Regulations to the European Patent Convention (CA/D 20/09)", Official Journal EPO dated Dec. 2009, dated Dec. 2009, pp. 582-584. http://archive.epo.org/epo/pubs/oj009/12_09/12_5829.pdf.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", http://www.merriam-webster.com/dictionary/froth, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

(56) References Cited

OTHER PUBLICATIONS

Hospira, "Plum A+™ Infusion System" as archived Dec. 1, 2012, pp. 2. www.hospira.com/products_and_services/infusion_pumps/plum/index.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
International Search Report and Written Opinion received in PCT Application No. PCT Application No. PCT/US2021/041891, dated Oct. 26, 2021 in 10 pages.
JMS Co., Ltd., "Infusion Pump: OT-701", Tokyo, Japan, 2002, pp. 4.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", https://www.elektronik.ropla.eu/pdf/stock/mcp/mta11200b.pdf, 1995, pp. 44.
Moghissi, Etie, MD, FACP, Face, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An *in Silico* Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS—Thomson Microelectronics, "L6219—Stepper Motor Drive", Datasheet, Dec. 1996, pp. 10.
SGS—Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

\* cited by examiner

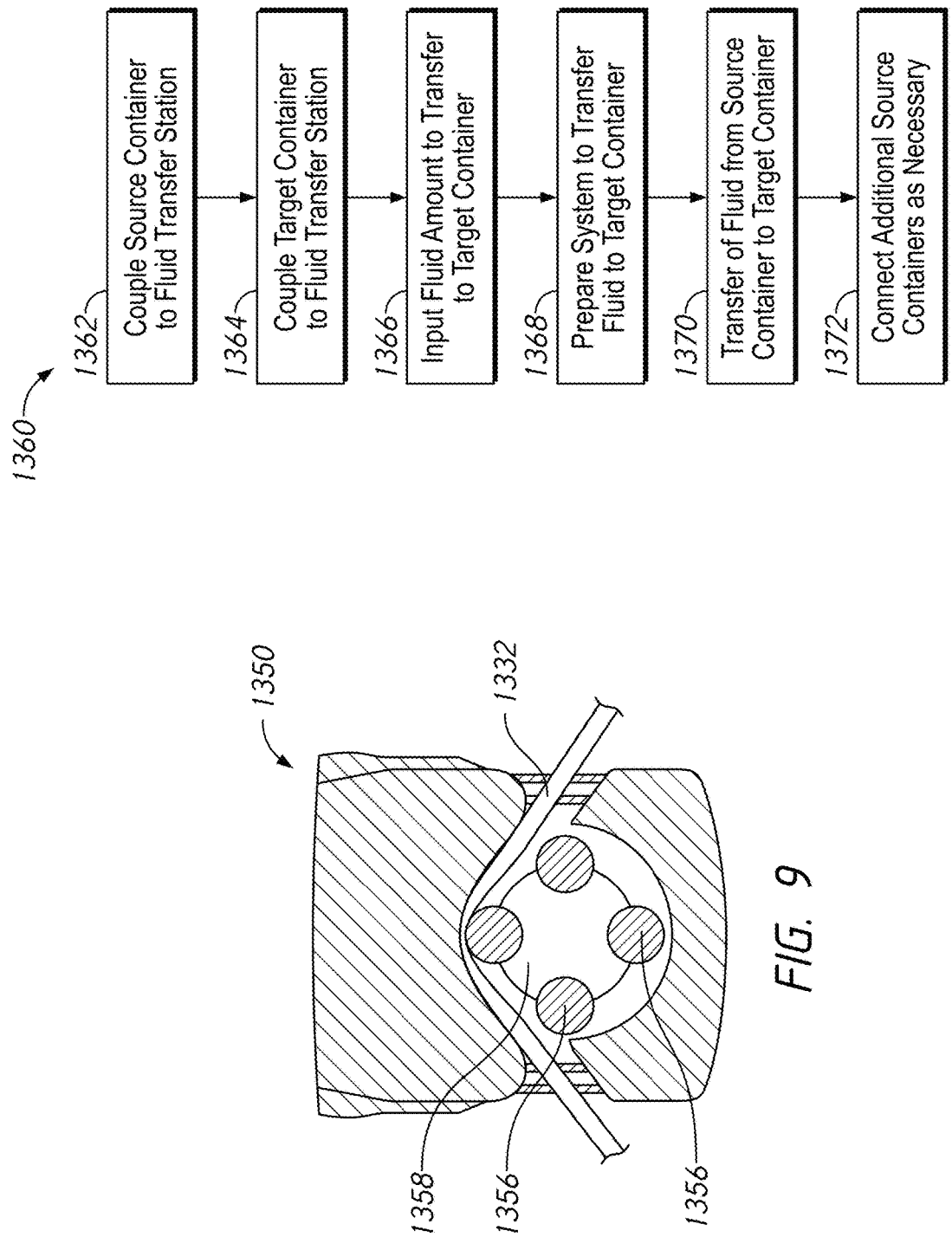

FIG. 18

FLUID TRANSFER DEVICES AND METHODS OF USE

CROSS-REFERENCE TO RELATED APPLICATION

This application is a continuation application of PCT Application No. PCT/US2021/041891 (the "'891 application"), filed Jul. 15, 2021, and titled FLUID TRANSFER DEVICES AND METHODS OF USE, which claims priority to U.S. Provisional Patent Application No. 63/054,568 (the "'568 application"), filed Jul. 21, 2020, and titled FLUID TRANSFER DEVICES AND METHODS OF USE, the contents of each of which are hereby incorporated by reference in their entireties and made part of this specification for all that they disclose.

INCORPORATION BY REFERENCE

U.S. Pat. No. 8,522,832 (the "'832 Patent"), titled "FLUID TRANSFER DEVICES AND METHODS OF USE," filed on Jul. 28, 2010 as U.S. patent application Ser. No. 12/845,548, and granted on Sep. 3, 2013, is hereby incorporated by reference in its entirety and made a part of this specification for all that it discloses.

U.S. Pat. No. 5,685,866 (the "'866 Patent"), titled "MEDICAL VALVE AND METHOD OF USE," filed on Nov. 4, 1994 as U.S. patent application Ser. No. 08/334,846, and granted on Nov. 11, 1997, is hereby incorporated by reference in its entirety and made a part of this specification for all that it discloses.

U.S. Pat. No. 7,998,134 (the "'134 Patent"), titled "MEDICAL CONNECTOR WITH CLOSEABLE MALE LUER," filed on May 8, 2008 as U.S. patent application Ser. No. 12/117,568, and granted on Aug. 16, 2011, is incorporated by reference in its entirety and made a part of this specification for all that it discloses.

U.S. Pat. No. 8,409,164 (the "'164 Patent"), titled "ANTI-REFLUX VIAL ADAPTORS," filed on Aug. 19, 2009 as U.S. patent application Ser. No. 12/543,776, and granted on Apr. 2, 2013, is hereby incorporated by reference in its entirety and made a part of this specification for all that it discloses.

U.S. Provisional Patent Application No. 61/557,793 (the "'793 application"), filed Nov. 9, 2011, and titled "MEDICAL CONNECTORS WITH FLUID-RESISTANT MATING INTERFACES," is hereby incorporated by reference in its entirety and made a part of this specification for all that it discloses.

PCT Patent Application No. PCT/US2012/054289, filed Sep. 7, 2012, and titled "MEDICAL CONNECTORS WITH FLUID-RESISTANT MATING INTERFACES," is hereby incorporated by reference in its entirety and made a part of this specification for all that it discloses.

U.S. Pat. No. 8,758,306 (the "'306 Patent"), titled "MEDICAL CONNECTORS AND METHODS OF USE," filed on May 12, 2011 as U.S. patent application Ser. No. 13/106,781, and granted on Jun. 24, 2014, is hereby incorporated by reference in its entirety and made a part of this specification for all that it discloses.

U.S. Pat. No. 9,883,987 (the "'987 Patent"), titled "FLUID TRANSFER DEVICES AND METHODS OF USE," filed on Jun. 20, 2014 as U.S. patent application Ser. No. 14/310,942, and granted on Feb. 6, 2018, is hereby incorporated by reference in its entirety and made a part of this specification for all that it discloses.

BACKGROUND

Field of the Disclosure

Some embodiments of the invention relate generally to devices and methods for transferring fluid and specifically to devices and methods for transferring medical fluids.

Description of the Related Art

In some circumstances it can be desirable to transfer one or more fluids between containers. In the medical field, it is often desirable to dispense fluids in precise amounts and to store and to transport potentially dangerous fluids. Current fluid transfer devices and methods in the medical field suffer from various drawbacks, including high cost, low efficiency, intensive labor demands, and excessive fluid or vapor leakage. Some embodiments disclosed herein overcome one or more of these disadvantages.

SUMMARY OF SOME EMBODIMENTS

Some embodiments disclosed herein relate to systems and methods for transferring fluid from source containers to target containers.

In some embodiments a medical fluid transfer system is provided. The medical fluid transfer system may comprise a pump configured to transfer fluid through a tube assembly having a first connector configured to couple to a source container and a second connector configured to couple to a target container. The medical fluid transfer system may also comprise a destination sensor configured to output information about the target container. The medical fluid transfer system may further comprise a control system. The control system may be configured to: receive an instruction to transfer a desired volume of a medical fluid to the target container; operate the pump based on the instruction and an operational setting associated with fluid volume; receive measurement data representing a measurement of the target container by the destination sensor (e.g., the weight of the target container after transfer of medical fluid to the target container); determine a difference between a transferred volume of the medical fluid and the desired volume of the medical fluid based at least partly on the measurement data and a fluid property of the medical fluid (e.g., specific gravity of the medical fluid); adjust the operational setting based on the difference; and operate the pump based on the operational setting that has been adjusted.

In some embodiments, the control system comprises a user interface, and the measurement data is received by the control system via the user interface. In some embodiments, the control system comprises a first communication interface, the destination sensor comprises a second communication interface, the destination sensor transmits the measurement data via the second interface, and the measurement data is received by the control system via the first communication interface. In some embodiments, the control system determines the transferred volume of medical fluid based on the specific gravity of the medical fluid and the weight of the target container. In some embodiments, the pump is a peristaltic pump comprising a rotor with one or more lobes. In some embodiments, the operational setting indicates a quantity of rotations that the rotor is to be rotated for transfer of one or more volumetric units of the medical fluid. In some embodiments, a plane of rotation of the rotor is substantially orthogonal to a direction of gravity during operation of the peristaltic pump. In some embodiments, the control system is further configured to manage a batch transfer operation in which the control system operates the pump to transfer the desired volume of the medical fluid to each of a plurality of target containers. In some embodiments, the control system is further configured to delay a subsequent segment of the batch transfer operation for a predetermined time interval after completion of a prior segment of the batch transfer operation.

BRIEF DESCRIPTION OF THE DRAWINGS

Certain embodiments of the invention will now be discussed in detail with reference to the following figures. These figures are provided for illustrative purposes only, and the embodiments are not limited to the subject matter illustrated in the figures.

FIGS. 7, 8, and 9 illustrate usage of an embodiment of a peristaltic pump.

FIG. 10 is a flow diagram of an example embodiment of a method for using an automated system for transferring fluid.

Figure 18:
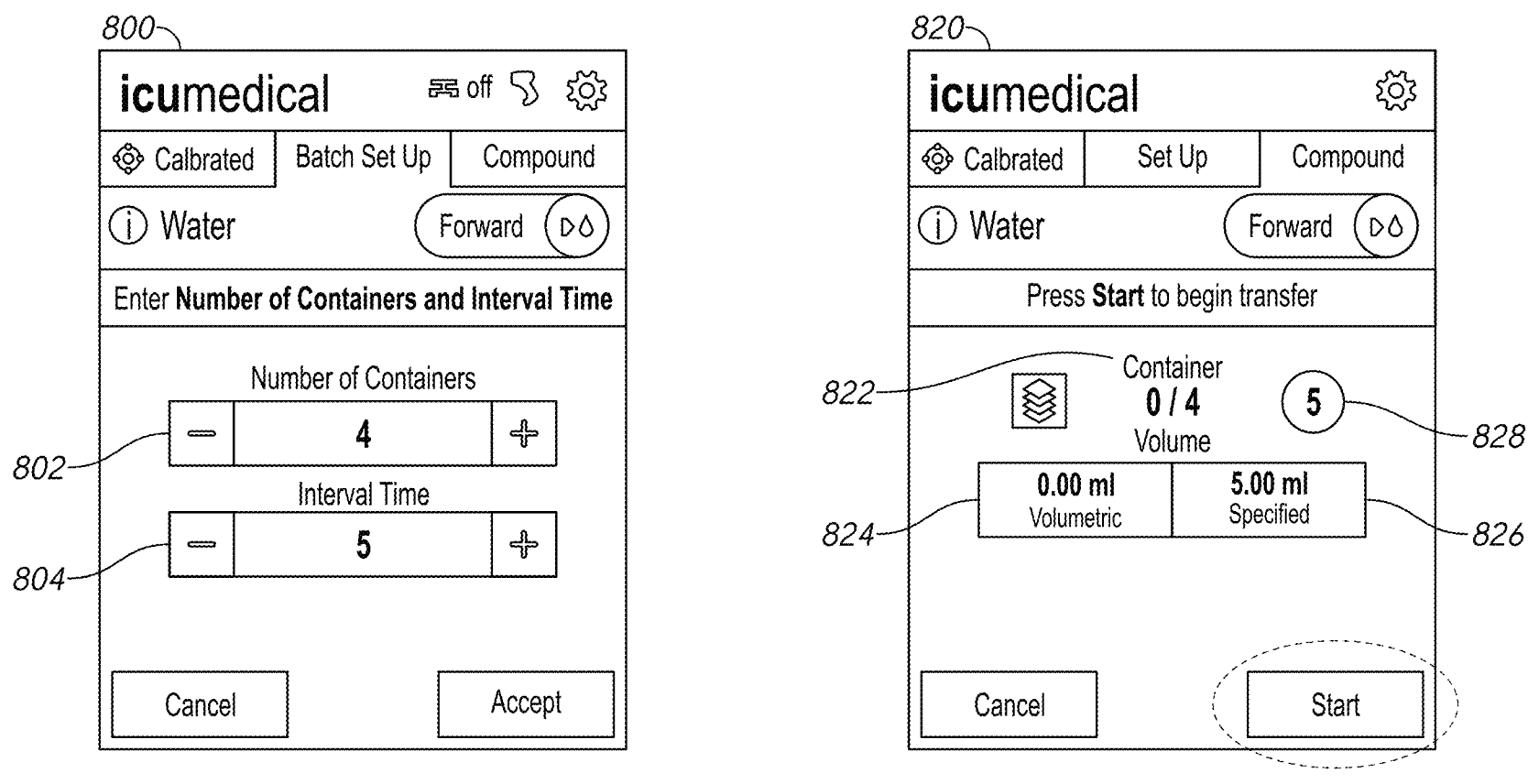

FIG. 18 is a view of user interfaces for managing the batch transfer of fluid with period verification using the system of FIG. 11.

DETAILED DESCRIPTION OF SOME EXAMPLE EMBODIMENTS

The following detailed description is now directed to certain specific example embodiments of the disclosure. In this description, reference is made to the drawings wherein like parts are designated with like numerals throughout the description and the drawings.

In many circumstances fluid is transferred from a source container to a target container. In some instances, it can be desirable to transfer precise amounts of a fluid, such as a medication, into the target container. For example, in some embodiments a medication can be stored in a vial or other container, and a precise dosage amount of the medication can be extracted and transferred to a target device so that the dosage amount can be delivered to a patient. In some embodiments, fluid from multiple source containers can be combined, or compounded, into a single target container. For example, in some embodiments a mixture of medications can be created in the target container, or a concentrated medication can be combined with a diluent in the target container. To achieve the desired proportions of fluids, it can be desirable to precisely measure the amounts of fluids transferred into the target container. Also, precisely measuring the amount of fluid transferred from the source container to the target container can reduce the amount of fluid wasted (e.g., when more fluid than necessary is withdrawn from the source container). Reduction of waste is desirable because, for example, in some instances the fluid being transferred can be expensive.

Some embodiments disclosed herein provide fluid transfer devices for transferring precise amounts of fluid from one or more source containers into one or more target containers.

In some embodiments, it can be desirable to transfer fluids from a source container to a target container using a sealed system. In some embodiments, exposing the fluid to ambient air can allow contaminants to enter the fluid or cause an undesirable reaction with the fluid. Some medications (e.g., chemotherapy medications) can be harmful to an unintended recipient. Therefore, it can be desirable to prevent or reduce exposure of the fluid being transferred to the ambient air or area outside the fluid transfer system. In some embodiments, a fluid transfer system that prevents or reduces exposure of the fluid to the area outside the fluid transfer system can render other expensive equipment (e.g., a clean room) unnecessary, thereby reducing the cost associated with transferring the fluids.

Some embodiments disclosed herein provide a fluid transfer device for transferring fluid while preventing, reducing, or minimizing the amount of contact the fluid has with the ambient air or area outside the fluid transfer system.

Figure 1A:
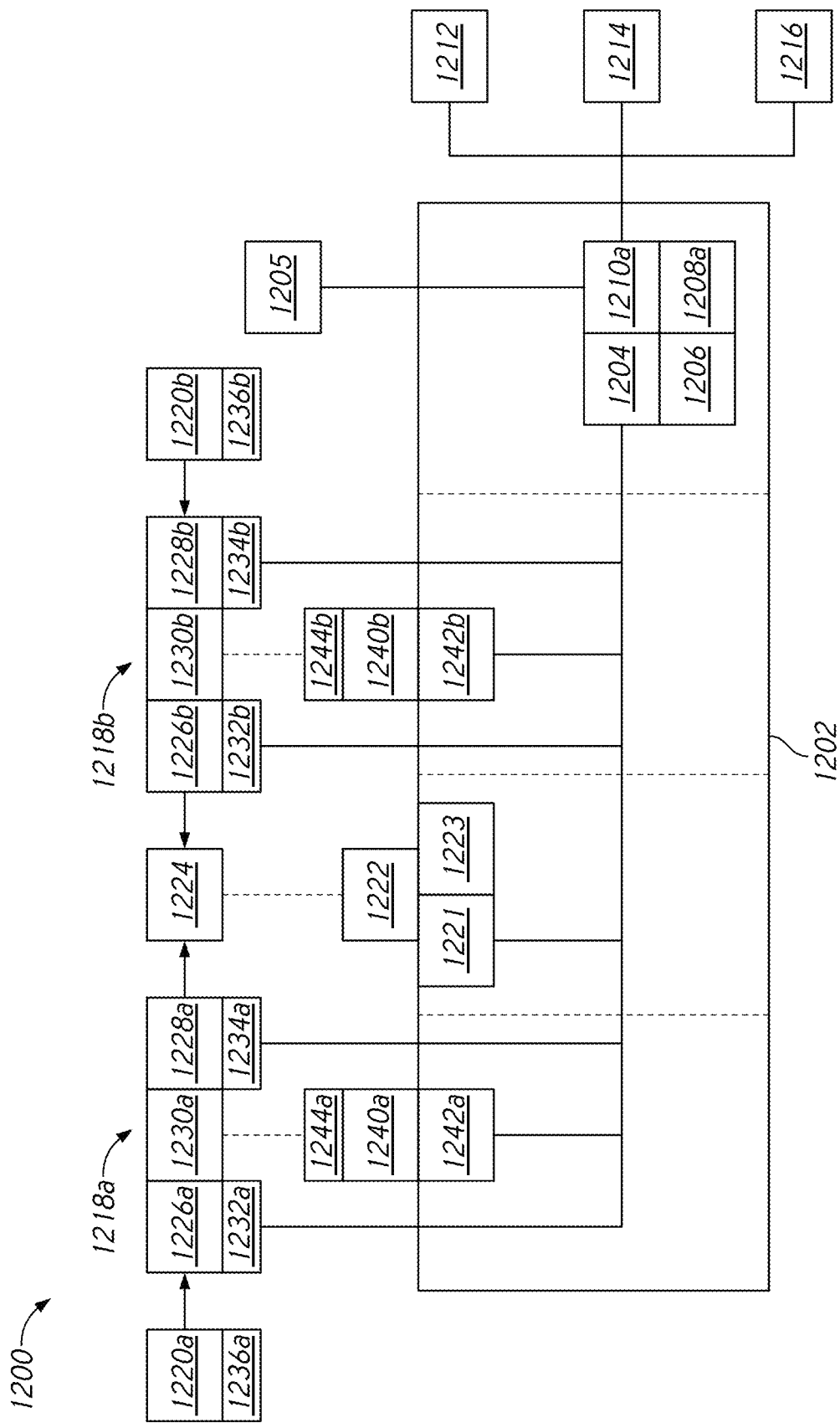
FIG. 1A schematically shows an example embodiment of an automated system for transferring fluid.

FIG. 1A schematically shows an embodiment of an automated fluid transfer system 1200. The system 1200 comprises one or more fluid transfer stations 1218a-b, a destination sensor, such as an end volume sensor or a weight sensor 1222, and a controller 1204. Although in the embodiment shown, the components are all contained within the housing 1202, a variety of other configurations are possible. For example, the system 1200 can include one or more housings 1202 enclosing components of the various systems. In some embodiments, each component grouping can have a separate housing (as illustrated by the dashed lines within the housing 1202). In some embodiments the controller 1204 can be contained within the same housing as the first fluid transfer station 1218a. In some embodiments there is a single fluid transfer station 1218a. In some embodiments there can be a plurality (e.g., a first and a second) of fluid transfer stations 1218a-b. In some embodiments the destination sensor 1222 can be in a different housing than the fluid transfer stations 1218a-b and the controller 1204. In some embodiments, the controller 1204 can be external to the housing 1202, and can be, for example contained within a second housing, which may also contain the user interface 1208.

The system 1200 has a controller 1204 and a memory module 1206. The controller 1204 can be configured to control the operation and functions of the fluid transfer stations 1218a-b and the destination sensor 1222. The system 1200 can also include a user interface 1208, which can be, for example, external to the housing 1202. The user interface 1208 can also be integrated into the housing 1202 in some cases. The user interface 1208 can include, for example, a display, a keypad, and/or a touch screen display. The user interface 1208 can be configured to receive instructions from the user, for example, regarding the amounts of fluid to be transferred and the types of fluids to be transferred. The user interface can also be configured to provide information to the user, such as error messages, alerts, or instructions (e.g., to replace an empty vial). In some embodiments, the system 1200 can include a communication interface 1210 configured to receive information (e.g., instructions) from a remote source such as an external controller 1212, a terminal (such as a computer) 1214, or an automated management system (such as a hospital information system (HIS)) 1216, etc. In some embodiments, the communication interface can also send information (e.g., results or alerts) to the remote source. The communication interface can include one or more connection types and can be configured to allow connectivity to multiple remote sources at once. In some embodiments, the system 1200 does not include a communication interface 1210 and does not communicate with a remote source.

The destination sensor 1222 can include a communication interface 1221 that can communicate with the controller 1204. In some embodiments a weight sensor 1222 can communicate with the controller using wireless communication. In some embodiments a weight sensor 1222 can be physically connected to the controller 1204 using a standard communication interface (e.g., RS232, USB, etc.). The controller 1204 can receive information (e.g., measurements, current state of operation, etc.) and provide commands (e.g., zeroing the weight sensor) to the weight sensor 1220 through the communication interface 1221. In some embodiments the weight sensor 1222 can include a user interface 1223. The user interface can provide a visual indication of weight, and other information. In some embodiments the weight sensor 1222 can receive commands or instructions through the user interface 1223 from a user.

The destination sensor 1222 is used to determine the amount of fluid transferred from the source container 1220a-b to the target container 1224. The destination sensor 1222 outputs the weight of the fluid transferred to the target container to the controller 1204. Prior to transferring fluid, the scale can be programmatically zeroed in order to compensate for the weight of the target container 1224. For example, a base weight can be assigned as "zero" fluid weight (i.e., equivalent to the weight of the inherent scale weight and/or equivalent to the inherent scale weight plus a first fluid weight, and/or equivalent to the weight of the target container). The scale can then determine the relative weight of the fluid transferred to the target container 1224 beyond the base weight.

In some embodiments, the destination sensor 1222 is a scale that is capable of receiving weight information and electronically providing the information to the controller 1204. The scale can be located in a separate housing 1202. In some embodiments, the scale can have a substantially flat weighing surface for the target container. In some embodiments (not illustrated) the scale can be a hanging scale.

In some embodiments, the fluid transfer station can include a positive displacement pump, such as a peristaltic pump, 1240a-b, a motor 1242a-b and a fluidics assembly. The positive displacement pump 1240a-b can be used to pump fluid from a source container 1220a-b to a target container 1224. The fluid is transferred via a hose 1228a-b fitted inside a pump mounting interface 1244a-b. A rotor with a number of lobes rotates and compresses the hose 1228a-b progressively along an advancing portion of the hose. As the lobe passes a particular portion of hose, such portion of hose rebounds to substantially its original shape and internal volume. As the rotor turns, the part of hose 1228a-b under compression is pinched, thus, displacing fluid and forcing the fluid to move forward through the tube. The speed of the rotation of the rotor, the number of lobes, and the material properties of the hose influence the flow rate of the fluid through the system. The flow rate of the fluid transfer can be controlled by varying the speed of the pump 1240a-b. The motor 1242a-b operating the pump 1240a-b can run at variable speeds. The peristaltic pump 1240a-b can be configured to operate at a low pressure. The pressure generated by the pump 1240a-b can be sufficiently low, such that it is below a threshold at which the connector 1230a-b will not leak if the pump is operating and the connector 1230a-b is not connected to the target container.

The operations of the pump can be controlled by the controller 1204. In some embodiments, the housing 1202 incorporating the pump can have a touch screen that allows commands to be provided to the controller 1204. For example, a user can instruct the pump to transfer a specific amount of fluid to the target container. In some embodiments the commands can be received from an external source such as a network computer. The controller 1204 can operate the pump at variable speeds by controlling the speed of the motor. The controller 1204 can control that rate at which the rotor is spinning, which, in turn, controls the fluid flow rate. In some embodiments, the computer can use an algorithm to reduce the speed of the motor as the amount of fluid approaches the desired amount of fluid in the target container in order to increase accuracy.

Each fluid transfer station 1218a-b can have a fluidics assembly that includes a first connector 1226a-b, a hose 1228a-b, and a second connector 1230a-b. The hose 1228a-b can be formed from a compressible material (e.g., silicone rubber, and other elastomeric materials). The hose 1228a-b is configured to be inserted within the mounting interface 1244a-b of the peristaltic pump 1240a-b (as illustrated by the dashed line) in order to facilitate the transfer of fluid between the source container 1220a-b and the target container 1224. Some embodiments can be assembled from different types or portions of hose. In some embodiments, the hose 1228a-b can be formed from a single material. In some embodiments, the hose is formed with an elastomeric portion and other portions formed from polymeric materials. The first and second connectors 1226a-b, 1230a-b are fixedly coupled to the hose 1228a-b at opposite ends and are not configured to be removable from the hose. The first connector 1226a-b is configured to connect to the source container 1220a-b. In some embodiments, one or more pairs of male and female fluid connectors configured to be attached to each other to selectively permit the passage of fluid between the source container 1220a-b and the target container 1224. The connectors can be detached or disconnected, for example, so that the target container 1224 can be removed once the fluid has been transferred. In some embodiments, the connectors can be configured to automatically close when disconnected from a corresponding connector, thereby preventing fluid from escaping when the connectors are detached. Thus, the fluid transfer system 1200 can be used to transfer fluid while retaining substantially entirely, or entirely, all of the fluid within the system, permitting the fluid transfer to occur in a substantially entirely, or entirely, closed system. The fluid transfer system 1200 can thereby reduce or eliminate the risk of injury, waste, or damage caused by liquid or vapor leakage when connecting and disconnecting the components of the fluid transfer system 1200.

Each transfer station 1218a-b can include a fluid source container 1220a-b, which can be, for example, a medical vial or other suitable container such as a bag, a bottle, or a vat, etc. Although many embodiments disclosed herein discuss using a vial as the source container, it will be understood the other containers can be used even when not specifically mentioned. In some embodiments, each of the source containers 1220a-b can contain a unique fluid, providing a variety of fluids that the user can select for transfer. In other embodiments, two or more of the source containers 1220a-b can contain the same fluid. In some embodiments, the source containers 1220a-b include bar codes that identify the types of fluid contained therein. The bar codes can be scanned by a bar code scanner 1205 that is in communication with the controller 1204 and/or the memory 1206 (e.g., via the communication interface 1210) so that the identities of the fluids contained by source containers 1220a-b can be stored within the memory module 1206. In some embodiments, the fluid transfer stations 1218a-b are configured to transfer precise amounts of fluid from source containers 1220a-b to a target container 1224, which can be, for example an IV bag. It will be understood that in various embodiments described herein, a different type of target container or destination container can be used instead of an IV bag (e.g., a syringe, a bottle, a vial, an elastomeric pump, etc.) even when not specifically mentioned.

In some embodiments, the system 1200 can include source adapters 1236a-b configured to receive the source containers 1220a-b and removably connect to the connectors 1226a-b. Thus, when a source container 1220a-c runs out of fluid, the empty source container 1220a-b and its corresponding adapter 1236a-b can be removed and replaced without requiring disengagement of the associated connector 1226a-b from the housing 1202. In some embodiments, source adapters 1236a-b can be omitted, and the source containers 1220a-b can be directly received by the connectors 1226a-b.

In some embodiments using two or more fluid transfer stations 1218a-b, the fluid transfer system 1200 can be used to transfer and combine individual fluids from the source containers 1220a-b to the target container 1224. The system 1200 can be used for compounding mixtures of fluids. For example, the system 1200 can be used to combine multiple medications together or to combine feeding fluids (e.g., water, dextrose, lipids, vitamins, minerals). The system 1200 can also be used to dilute a medication or other fluid to a desired concentration level. In some embodiments, a first fluid transfer station 1218a can include a concentrated medication or other fluid, and a second fluid transfer station 1218b can include saline or other diluent. The system 1200 can be configured to receive input (e.g., from a user or from a hospital information system) indicating a desired amount and concentration of medication, and the system 1200 can be configured to transfer the precise amounts of the concentrated medication and the diluent required to fill the source container 1224a with the desired amount and concentration of the medication. The system can calculate the amount that needs to be transferred from each fluid transfer station 1218. The operation can then be done serially by transferring a first fluid from the first transfer station 1218a and then separately transferring a second fluid from the second transfer station 1218b. In some embodiments, a technician can manually connect the first fluid transfer station 1218a, via connector 1230a, to the target container 1224. After the first fluid is transferred the connector 1230a is disconnected and second fluid transfer station is connected, via connector 1230b, to the target container 1224 to transfer the second fluid. In some embodiments, the system 1200 can include an actuator that is capable of automatically switching the connection of the target container 1224 between the fluid transfer stations 1218a-b. In some embodiments, the actuator can switch between different fluid sources at the same fluid transfer station. For example, the first fluid source can be a concentrated medication or other fluid, and a second fluid source can be saline or some other diluent.

In some embodiments, the system 1200 can include compatibility modules 1232a-b for permitting connections with approved connectors 1226a-b, and for preventing connectors other than approved connectors 1226a-b from being placed in communication with the system 1200. The compatibility modules can be, for example, a specifically shaped mounting feature (e.g., on the housing of the fluid transfer station) that is configured to interface with a corresponding portion of the connector 1226a-b, 1230a-b. In some embodiments, the compatibility modules 1232a-b can be one or more sensors configured to detect the presence of an approved connector 1226a-b or to align with a specific portion of the connector 1226a-b during operation.

In some embodiments the system 1200 can include sensors 1234a-b for detecting the presence of the target container 1224. Sensors 1234a-b can be in communication with the controller 1204 so as to prevent the system 1200 from attempting to transfer fluid when no target container 1224 is connected. A variety of sensor types can be used for sensors 1234a-b. For example, sensors 1234a-b can be weight sensors, sensor pads, infrared sensors, or other forms of electronic sensors. In some embodiments, the sensor 1234a-b can align with a substantially transparent portion of the connector 1226a-b to detect whether a valve on the connector 1226a-b leading to target container 1224a-b is open. If open, the sensor 1234a-b can send a signal to the controller 1204 so that fluid transfer is permitted. The sensors 1234a-b can be configured to align properly with only approved connectors 1226a-b so that the sensors 1234a-b do not allow fluid transfer if an unapproved connector is used. Thus, the sensors 1234a-b can be used as the compatibility modules 1232a-b in some embodiments.

The fluid transfer system 1200 can have many different configurations. For example, in some embodiments there is only a single fluid transfer station. In some embodiments, certain features shown in FIG. 1A can be omitted for some or all of the transfer stations. For example, in some embodiments, a fluid transfer station can have the sensors omitted because, for example, a particular peristaltic pump does not generate sufficient pressure to cause fluid to leak out the connector when a target container is not connected and the pump is running.

Figure 1B:
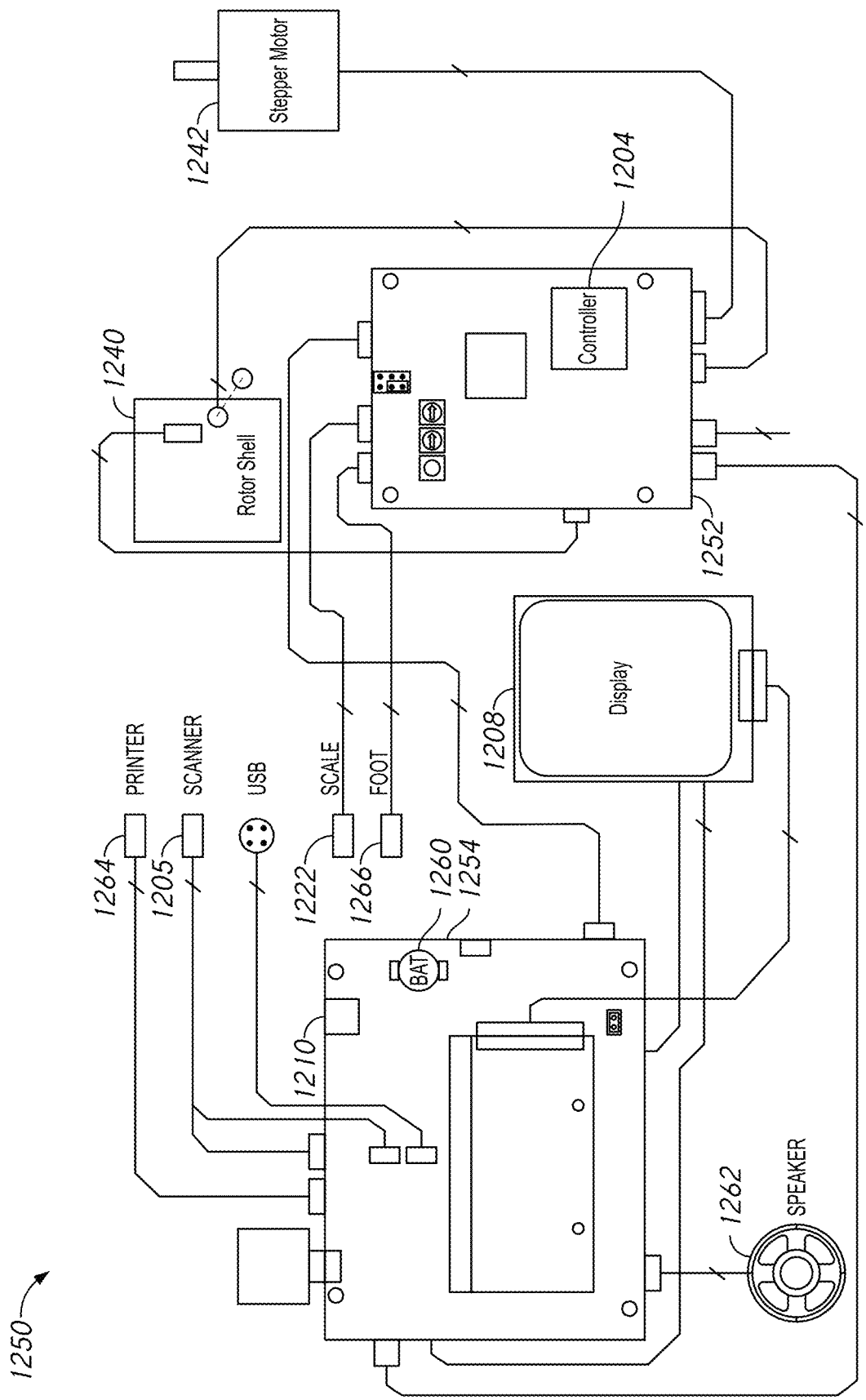
FIG. 1B schematically shows another example embodiment of an automated system for transferring fluid.

FIG. 1B illustrates an example embodiment of a fluid transfer system 1250 in a configuration that can have features similar to, or the same as, the example fluid transfer system 1200 shown in FIG. 1A. For example, the system 1250 may include one or more fluid transfer stations that each comprise a peristaltic pump 1240 and a motor 1242 to transfer fluid from a source container to a target container, as described in greater detail herein. The system 1250 has a controller 1204 that can be configured to control the operation and functions of one or more fluid transfer stations. The fluid transfer system 1250 can include one or more circuit boards, such as boards 1252 and 1254. The circuit boards 1252, 1254 may support the controller 1204 any of a variety of electronic components, such as any or all of the electronic components of the fluid transfer system 1200 shown in FIG. 1A, by providing power, communications, and the like.

The system 1250 can also include a user interface 1208, such as a display, a keypad, and/or a touch screen display. The user interface 1208 can be configured to receive instructions from the user, for example, regarding the amounts of fluid to be transferred and the types of fluids to be transferred. The user interface can also be configured to provide information to the user, such as error messages, alerts, or instructions (e.g., to replace an empty vial).

In some embodiments, the system 1250 can include a communication interface 1210 configured to receive information (e.g., instructions) from a remote source such as an external controller, a terminal (such as a computer), or an automated management system (such as an HIS), etc. In some embodiments, the communication interface 1210 can also send information (e.g., results or alerts) to the remote source. The communication interface 1210 can include one or more connection types and can be configured to allow connectivity to multiple remote sources at once. In some embodiments, the system 1250 does not include a communication interface 1210 and does not communicate with a remote source.

The fluid transfer system 1250 may also include a weight sensor 1222 to assist in evaluating the transfer of fluid to and/or from a container, such as a source container or target container. The fluid transfer system 1250 may also include a bar code scanner 1205 for input of data from medication containers, patient charts, or the like.

The fluid transfer system 1250 may include one or more components in addition to, or instead of, those of the fluid transfer system 1200. In some embodiments, as shown, the fluid transfer system 1250 may include a battery 1260 to provide primary power, or to provide backup power in the event of disconnection from—or otherwise loss of power from—a primary power source. The fluid transfer system 1250 may include a speaker 1262 to provide audible feedback, alerts, etc. The fluid transfer system 1250 may include a printer 1264 to print hard copies of information, such as labels for medication, barcodes, and the like. The fluid transfer system 1250 may include a pedal 1266 to provide input, such as start or stop commands. These components may be coupled to or otherwise in electronic communication with one or more circuit boards 1252, 1254.

The fluid transfer system 1250 can have many different configurations. For example, in some embodiments there is only a single fluid transfer station. In some embodiments, certain features shown in FIG. 1B can be omitted for some or all of the transfer stations.

Figure 2:
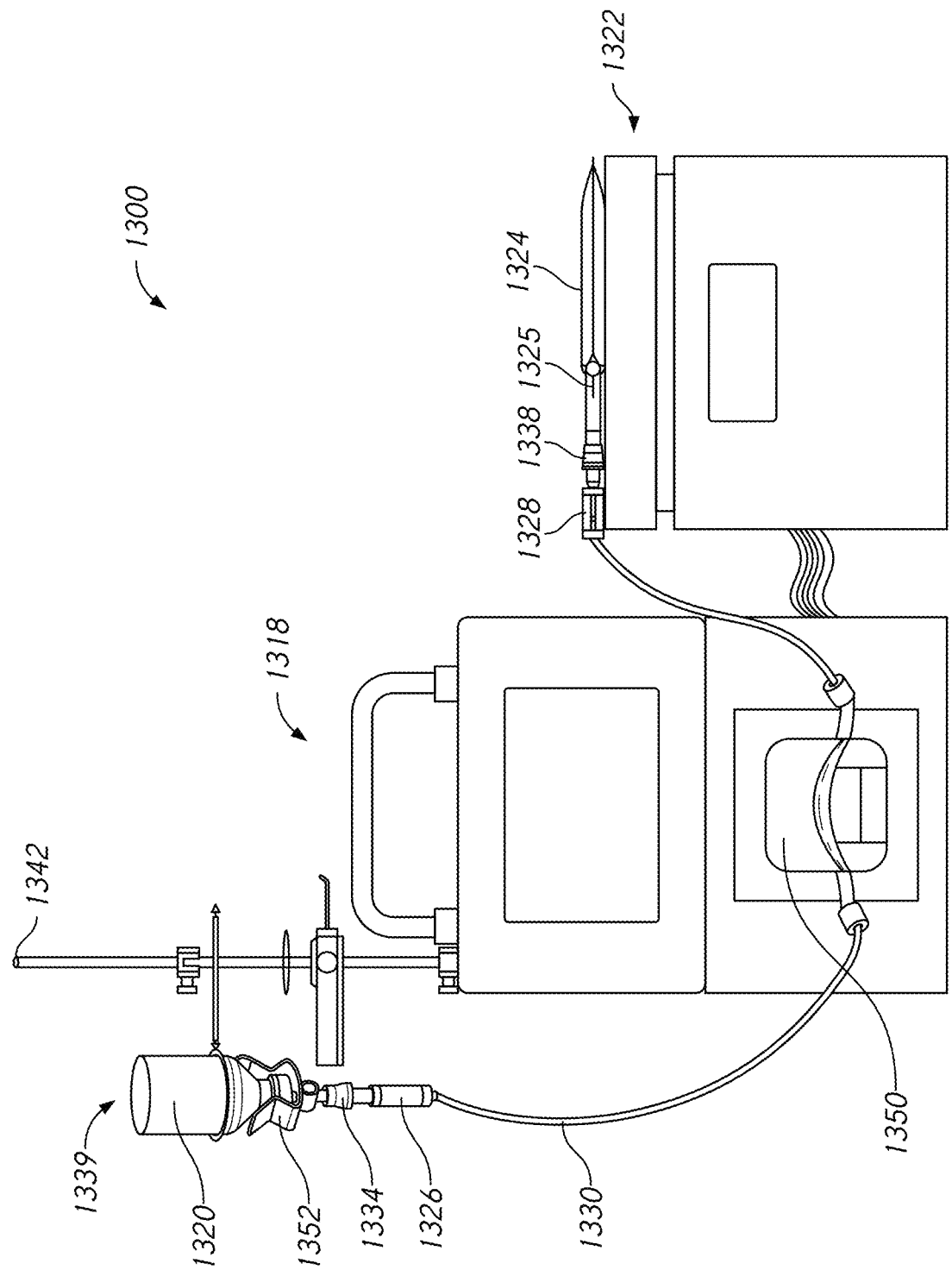
FIG. 2 is a view of an example embodiment of an automated system for transferring fluid.
Figure 4:
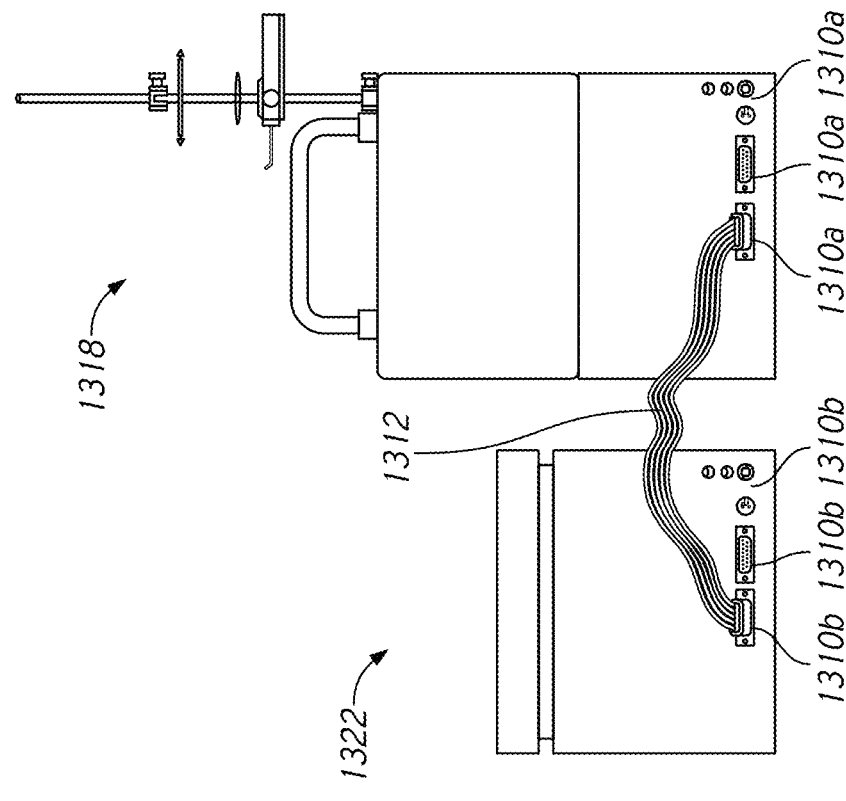
FIG. 4 is a back view of the system of FIG. 2.
Figure 3:
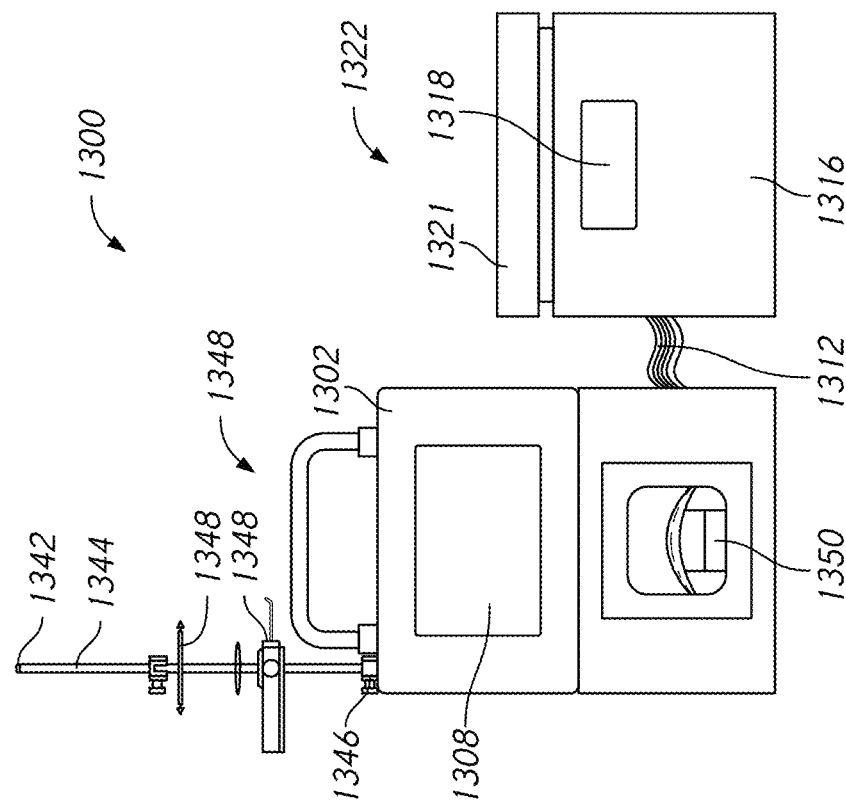
FIG. 3 is a front view of the system of FIG. 2.

FIG. 2 is an example embodiment of a fluid transfer system 1300, which can have features similar to, or the same as, the systems 1200 and/or 1250 described above or any other fluid transfer system described herein. FIG. 3 is a front view of the fluid transfer system 1300 and FIG. 4 is a back view of the fluid transfer system 1300. In FIGS. 3 and 4, certain features (i.e., the fluidics assembly) are omitted from view. The system 1300 can include a fluid transfer station 1318 and a weight sensor 1322.

The fluid transfer station 1318 includes a housing 1302, a peristaltic pump 1350, a motor (not shown), a user interface 1308, and a pole assembly 1342. The user interface 1308 can be incorporated into the housing. The user interface 1308 can include a touchscreen, a keypad, a display, or other suitable interface devices for providing information to a user and/or for providing input from the user to a controller (not shown).

As can be seen in FIG. 4, the fluid transfer station 1318 and the weight sensor 1322 can have communication interfaces 1310a-b. The communications interfaces 1310a-b can include one or more connection points to receive cables from one or more remote sources such as a remote terminal (e.g., a computer) or an automated management system (e.g., a hospital information system (HIS)). The fluid transfer station 1318 and the weight sensor 1322 have a communication link established between them, such as by cable 1312. In some embodiments the weight sensor 1322 and the fluid transfer station can establish a communication using wireless signal.

In some embodiments, the communication interfaces 1310a-b can be configured to provide a communication link between the system 1300 (i.e., the fluid transfer station and the weight sensor) and a remote location. The communication link can be provided by a wireless signal (e.g., using an antenna) or by one or more cables or a combination thereof. The communication link can make use of a network such as a WAN, a LAN, or the internet. In some embodiments, the communication interfaces 1310a-b can be configured to receive input (e.g., fluid transfer commands) from the remote location and/or can provide information (e.g., results or alerts) from the system to the remote location.

The fluid transfer station 1318 can be configured to transfer fluid from a vial 1320 to an IV bag 1324 using a peristaltic pump 1350. The fluid is transferred from the vial 1320 through a connector 1326, and into a hose assembly 1330. The peristaltic pump 1350 moves the fluid from the hose assembly 1330 through the connector 1328 and into the IV bag 1324. The operation of the peristaltic pump 1350 is controlled by the controller based on commands or information received from a user. An example of the fluidics assembly is described in additional detail below with additional reference to FIGS. 5 and 6. Operation of an embodiment of a peristaltic pump is described in additional detail below with reference to FIGS. 7 through 9.

The fluid transfer station 1318 can include a pole assembly 1342, which can be configured to hold fluid containers such as vials and fluid bags. A pole 1344 can extend upward from the housing 1302, and in some embodiments, the pole 1344 can be height adjustable and a thumb screw 1346 can be tightened to hold the pole 1344 in place. The thumb screw 1346 can be loosened to enable adjustment of the height of the pole 1344, and in some embodiments, the pole 1344 can be lowered into a recess formed in the housing 1302 that is configured to receive the pole 1344. the pole 1344 can be entirely, substantially entirely, or mostly withdrawn into the housing 1302 when the pole 1344 is not in use (e.g., during storage or transportation or when not needed to support fluid containers). One or more support modules 1348 can be attached to the pole 1344 and can be configured to support fluid containers. The support modules 1348 can include thumb screws so that the positions of the support modules 1348 on the pole 1344 can be adjustable, and/or so that the support modules 1348 can be removable from the pole 1344. In the illustrated embodiment, the support module 1348 can have one or more curved arms for supporting a fluid container such as vial 1320.

In some embodiments, the weight sensor can include a housing 1316, a user interface, and a weighing surface 1321. The user interface 1308 can be incorporated in the housing 1316. The user interface 1308 can provide a visual indication of weight, and other information. In some embodiments the weight sensor 1322 can receive commands or instructions through the user interface 1308 from a user. In some embodiments the weight sensor 1322 does not include a user interface 1308. The weighing surface 1321 is configured to provide a surface for the IV bag. The weighing surface 1321 can be sized so that the IV bag 1324 or other target container can be properly balanced and positioned on the weight sensor.

The weight sensor 1322 can provide information to (e.g., measurements, current state of operation, etc.) and receive commands (e.g., zeroing the weight sensor) from the fluid transfer station 1318 through the communication interface 1310*b*. The weight sensor 1322 is used to determine the amount of fluid transferred from the vial 1320 to the IV bag 1324.

Figure 5:
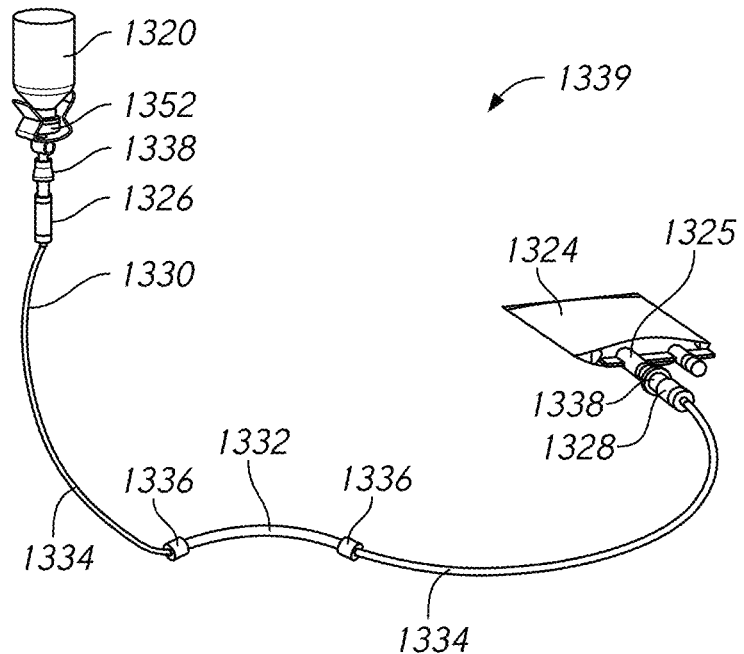
FIG. 5 is a perspective view of an example embodiment of a fluidics assembly that can be used to transfer fluid.
Figure 6:
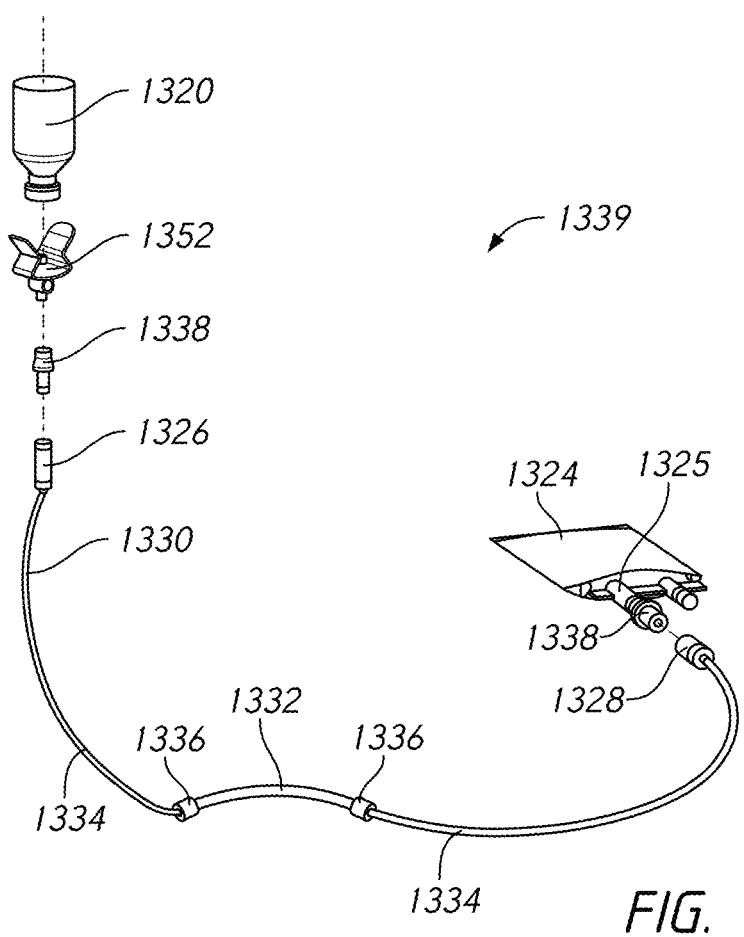
FIG. 6 is an exploded view of the fluidics assembly of FIG. 5.

FIG. 5 is a perspective view of a fluidics assembly 1339 that can be used with the fluid transfer station 1318. FIG. 6 is a perspective exploded view of the fluidics assembly 1339 shown in FIG. 5. The fluid assembly 1339 can be used to transfer precise amounts of fluid from a vial 1320 to an IV bag 1324. The fluidics assembly 1339 includes a vial 1320, a vial adapter 1352 configured to provide fluid communication with the fluid (e.g., chemotherapy drug or other medication) contained within the vial 1320 to a connector 1326, a tubing assembly 1330, a connector 1328, and the IV bag assembly 1324. In some embodiments, the fluidics assembly 1339 can be configured to allow the vial 1320 and vial adapter 1352 to be replaced (e.g., when the vial runs out of fluid) without replacing the connector 1326 or the tubing assembly 1330. In some embodiments, the vial adapter 1352 can be configured to allow air to enter the vial 1320 via the vial adapter 1352, thereby substantially equalizing pressure in the vial 1320 as fluid is drawn out.

A tubing or hose assembly 1330 can extend between the connector 1326 and the connector 1328. The tubing assembly includes first tube portions 1334, a second tube portion 1332, and tubing connectors 1336. The second tube portion 1332 is configured to be inserted within the peristaltic pump 1350. In some embodiments the second portion 1332 can be configured to be more flexible than the first portion 1334. In some embodiments the second tube portion 1332 can be configured to have a lower durometer value than the first portions 1334. In some embodiments, the second portion 1332 can be more compressible than the first portion 1334 at a given force. In some embodiments, the tube 1332 can be formed from silicone rubber, or other appropriately formed elastomeric materials. The tube portions 1334 are positioned between the connectors 1326, 1328 and the tubing connectors 1336. In some embodiments the first tube portions 1334 can be smaller diameter tubing than is used for the second tube portion 1332. The tubing connectors 1336 are configured to create a fluid tight seal between the second tube portion 1332 and the first tube portions 1334. In some embodiments, there are no first tube portions 1334 or tubing connectors 1336 and the second tube portion 1332 is coupled to the connector 1326 and the connector 1328.

A connector 1326 (e.g., a Spiros® closeable male connector or a first Chemolock™ connector manufactured by ICU Medical, Inc., of San Clemente, California) can be located at the end of the tubing assembly 1330 and can be used to connect to a corresponding connector 1338 (e.g., a Clave® connector or a second Chemolock™ connector manufactured by ICU Medical, Inc., of San Clemente, California) that is attached to the fluid source container 1320. Additional details relating to Clave® connectors and some variations are disclosed in the '866 Patent. In various embodiments disclosed herein, other types of connectors can also be used, such as a MicroCLAVE® connector (manufactured by ICU Medical, Inc., of San Clemente, California), or any other connector disclosed or described herein, including those in the '306 Patent, including, for example, clear connectors. When the connectors 1326 and 1338 are engaged, a fluid connection exists between the fluid source container 1320 and the connector 1326. A tube 1330 can extend from an outlet of the connector 1326 to a connector 1328 (e.g., a Spiros® closable male connector) which can be positioned at the opposite end of the tubing assembly 1330. A corresponding connector 1338 (e.g., a Clave® connector) can engage the connector 1328. The IV bag 1324 may have a supplemental line of tubing 1325 that can be configured to engage the connector 1338 to provide a fluid connection between the connector 1328 and the IV bag 1324.

Figure 8:
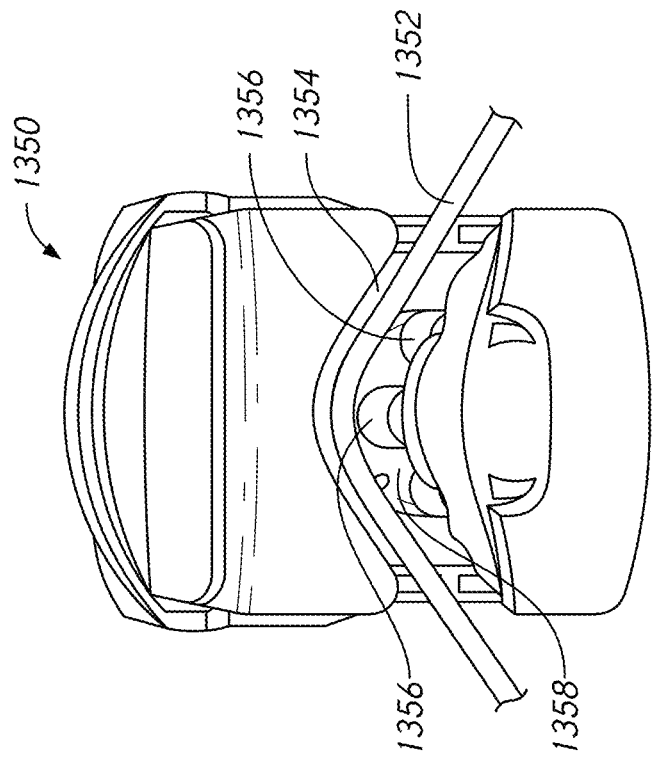
Figure 7:
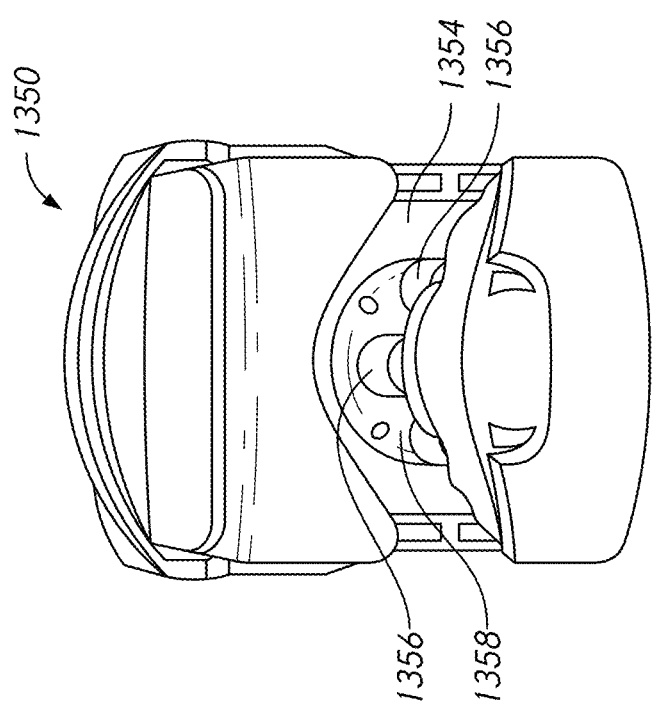

FIGS. 7 through 9 illustrate an embodiment of a peristaltic pump 1350 used by the fluid transfer station 1318. The peristaltic pump has a cover (not shown), a mounting interface 1354, a plurality of lobes 1356, a rotor 1358, and a motor (not shown). The peristaltic pump is a positive displacement pump used for pumping fluid from the vial 1320 to the IV bag 1324. The fluid is transferred via a compressible tube 1332 fitted inside the mounting interface 1354. The rotor 1358 has a plurality of lobes 1356 attached to the external circumference of the rotor compresses the flexible tube. In some embodiments the lobes can be rollers, shoes, wipers, or other members that facilitate the operation of the pump. As the rotor 1358 turns, the part of tube under compression is compressed, or occludes, thus forcing the fluid to be pumped to move through the tube. As the tube 1332 opens to its natural state after the passing of the lobes 1356 fluid flow is induced.

In some embodiments, the motor may rotate the rotor 1358 in a single direction (e.g., only clockwise, or only counterclockwise). Thus, the fluid may be pumped through the tube in a single direction, from a first end that is always coupled to a source container (e.g., a vial, medical fluid bag, or other suitable container) to a second end that is always coupled to a target container (e.g., an IV bag, an elastomeric pump, a syringe, or other suitable container).

In some embodiments, the motor may be configured to rotate the rotor 1358 in both a clockwise and counterclockwise direction. Thus, a first end of the tube may be coupled to a source container when the rotor 1358 is rotating in one direction (e.g., clockwise) and coupled to a target container when the rotor 1358 is rotating in a different direction (e.g., counterclockwise). For example, the motor may rotate the rotor 1358 in a first direction to move fluid from a source container to a target container. When the transfer is substantially complete, the motor may reverse directions and rotate the rotor 1358 in the second direction for a short time to depressurize or decompress the tube such that the pressure is sufficiently low and fluid is not urged outside of the tube upon disconnection of the target container. As another example, the source container may serve initially as a target container, such as when the source container includes lyophilized medication. The container with lyophilized medication may be coupled to a first end of the tube, and a container with a diluent (e.g., saline or sterile water) may be coupled to a second end of the tube. The motor may initially rotate the rotor 1358 in the first direction to move diluent into the container with the lyophilized medication. After the lyophilized medication is sufficiently hydrated, the motor may be stopped, and a new target container may be coupled to the end of the tube to which the diluent container was coupled (or the diluent container may remain coupled to the tube to now serve as a target container). The motor may then begin rotating the rotor in the second direction to move hydrated medication into the new target container.

In some embodiments of the pump 1350, the cover (if present) is opened, the tube 1332 is positioned within the mounting interface 1354 (see FIG. 8), and the cover is closed. FIG. 9 illustrates the tubing 1332 mounted within the pump 1350 during operation. As shown the peristaltic pump lobes pinch the tube and compress the tubing, thereby moving fluid through the tube 1332.

The flow rate of the fluid through the pump 1350 can be controlled by the speed of the pump motor. The motor can be a variable speed motor and the fluid flow rate can be precisely controlled by varying the speed of the motor.

The peristaltic pump can operate at low pressures, and can avoid building up high pressures if the tubing is not connected to the IV bag. The pressures can be sufficiently low that the connector 1328 does not leak when it is closed and the pump is operating and connected to a fluid source, such as the vial 1320. In some embodiments, the system does not include sensors for detecting the presence of a target container.

Additionally, the system does not include sensors, in some embodiments, for detecting air bubbles because the system uses the weight of the target container to determine when the correct amount of fluid is transferred. The pump can continue to operate until the desired amount of fluid has been transferred to the target container.

FIG. 10 is an example of a flowchart for a method of using a fluid transfer system to transfer fluid from a source container to a target container 1360. The fluid transfer system can use the same or similar components as the fluid transfer systems 1200, 1250, and 1300 described herein. At block 1362, source container (e.g., a medical vial or other suitable container such as a bag, a bottle, or a vat, etc.) is coupled to a fluid transfer station. The source container contains fluid (e.g., chemotherapy drug or other medical fluid). The source container can have a compatible adapter device. The source container is in fluid communication with a tubing assembly. The tubing assembly is in fluid communication with a target container (e.g., an IV bag, an elastomeric pump, a syringe, or other suitable container). The tubing assembly can be a closed system that retains substantially entirely, or entirely, all of the fluid within the assembly, permitting the fluid transfer to occur in a substantially entirely, or entirely, closed system. A closed system can reduce or eliminate the risk of injury, waste, or damage caused by liquid or vapor leakage when connecting and disconnecting the components of the fluidics system. The source container can be mounted on a fluid transfer station. The fluid transfer station can include a housing that incorporates a peristaltic pump, controller, user interface, and communication interface. The tubing assembly has a portion of tubing mounted within a peristaltic pump.

At block 1364 a target container (such as an IV bag, an elastomeric pump, a syringe, or other appropriate target container) is coupled to the opposite end of the tubing assembly. In some embodiments, the target container may be positioned on a weight sensor. The weight sensor is configured to weigh the target container to determine the amount of fluid that is transferred into the target container. The weight sensor can be incorporated in a separate housing from the fluid transfer station. The weight sensor can have a communication interface and can be in communication with the controller. The weight sensor can provide information to the controller and receive instructions from the controller.

At block 1366, the fluid transfer station receives a command to transfer a specific amount of fluid from the source container to the target container. A user can provide commands through the user interface on the fluid transfer station. In some embodiments the commands can be received by a remote source. The user can identify a specific amount of fluid that is to be transferred (e.g., 10 ml, 30, ml, 100 ml, etc.) to the target container. After determining the amount of fluid to be transferred, the user can instruct the fluid transfer system to proceed with the transfer. In some embodiments the fluid transfer system can verify that the user has entered in the correct amount of fluid to be transferred.

At block 1368, the fluid transfer station processes the commands and prepares the system to transfer the fluid to the target container. The controller zeros the weight sensor to compensate for other masses in the system, such as the weight of the target container assembly. This allows the scale to determine the amount of fluid that will be transferred to the target container. After the scale has been zeroed the controller can initiate the transfer of fluid to the target container.

At block 1370, the controller instructs the motor of the peristaltic pump to operate pumping until the weight of the scale meets the specified weight of transferred fluid in the target container. The motor can vary the speed of the peristaltic pump based on the amount of fluid to transfer to the target container. As the amount of fluid approaches the specified amount, the speed of the motor can slow down, thereby reducing the flow rate of fluid into the target container, in order to increase accuracy. The controller can use an algorithm to determine the appropriate speeds at which to operate the pump. In some embodiments the controller can determine the flow rate associated with different speeds of the motor. The controller will continue to operate the motor until the specified amount has been transferred to the target container.

At block 1372 additional source containers can be coupled to the fluid transfer station. The source containers can continue to be replaced until the specified amount of fluid has been transferred to the target container. In some embodiments the motor can stop when the controller detects that the source is disconnected. In other embodiments the pump continues to operate until the specified weight is achieved regardless of whether the source container is disconnected. In some embodiments the controller can determine that fluid is not being transferred from the source container to the target container. In some embodiments the controller can receive input from a sensor to determine whether the source container is empty. In some embodiments the controller can determine that fluid is not being transferred from the source container because the motor is operating but fluid is not being transferred. In such instances, the controller can provide an audible alarm to the user, stop the operation of the motor, and/or perform other appropriate actions. A reservoir container can be used to transfer the contents of multiple source containers to the reservoir container prior to transferring the fluid to the target container.

Figure 11:
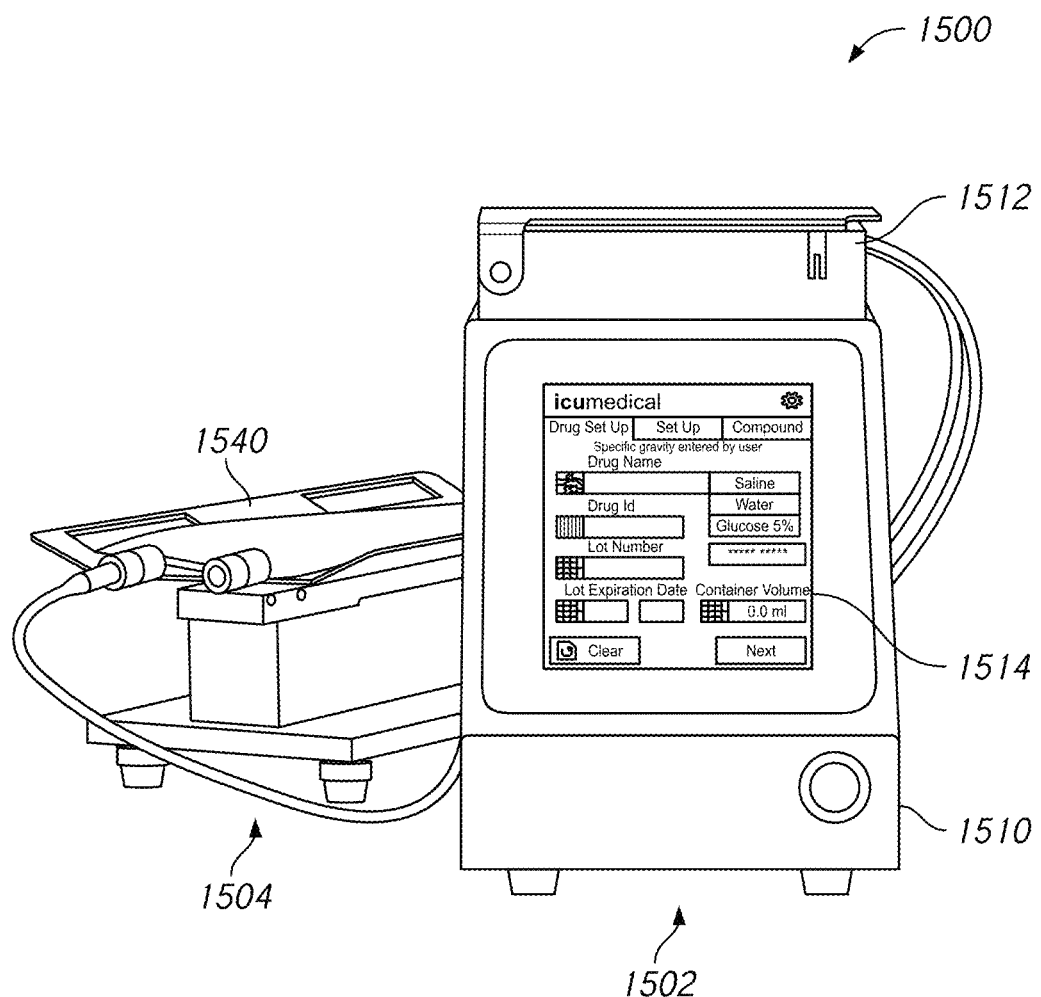
FIG. 11 is a view of another example embodiment of an automated system for transferring fluid.

FIG. 11 is an example embodiment of a fluid transfer system 1500, which can have features similar to, or the same as, the systems 1200, 1250, or 1300 described above or any other fluid transfer system described herein. The system 1500 can include a fluid transfer station 1502 and various auxiliary devices. For example, the system 1500 may include a destination sensor, such as a weight sensor 1504. As another example, the system 1500 may include a foot pedal (not shown). The fluid transfer station 1502 may communicate with the weight sensor 1504 and/or foot pedal via communication interfaces (not shown) in the respective devices. In some embodiments, the communication interfaces may be wired communication interfaces configured to be coupled to—and communicate via—a cable or other physical transmission medium between devices. In some embodiments, the communication interfaces may be wireless communication interfaces configured to transmit and receive wireless signals. In some embodiments, communication between components of the system 1500 and/or to external systems (other fluid transfer systems, a hospital information system, etc.) may be provided using any of the communication interfaces or features described above with respect to the fluid transfer system 1300.

Figure 13:
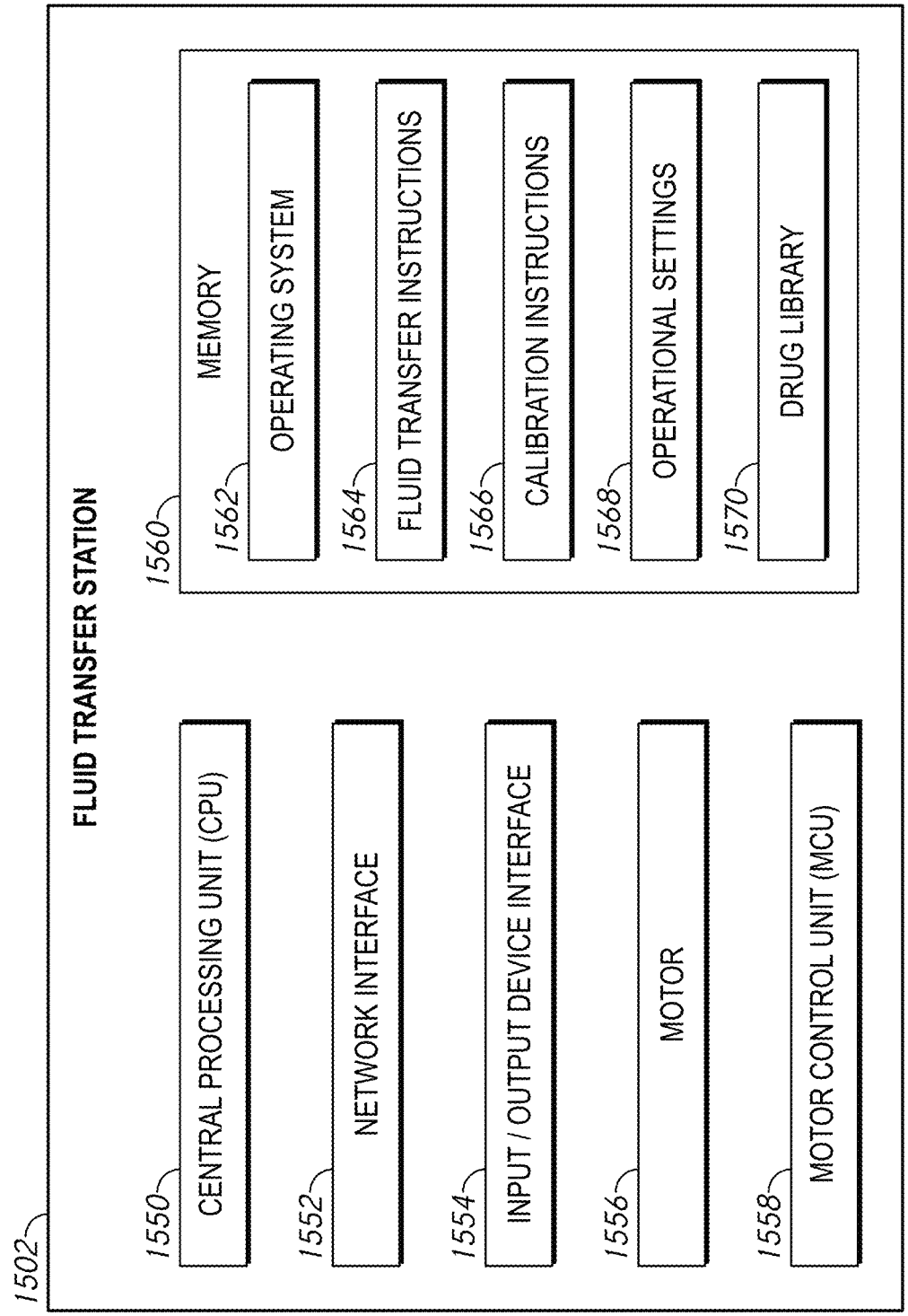
FIG. 13 schematically shows components of the system of FIG. 11.

As shown, the fluid transfer station 1502 may include a housing 1510, a peristaltic pump 1512 to effectuate the transfer of fluid from a source container to a target container, and a user interface 1514. The user interface 1514 can include a touchscreen, a keypad, a display, a microphone, a speaker, and/or other suitable interface devices for providing information to a user and/or for providing input from the user to a controller (not shown). Examples of user interface displays to manage various operations of the system 1500 are described in greater detail below. The user interface 1514 can be incorporated into the housing 1510. The fluid transfer station 1502 may also include various internal components as shown in FIG. 13 and described in greater detail below.

The weight sensor 1504 may have features similar to, or the same as, the weight sensor 1322. In some embodiments, the weight sensor 1504 can include a user interface (not shown) and a weighing surface 1540. The user interface can provide a visual indication of weight, and other information. In some embodiments the weight sensor 1504 can receive commands or instructions through the user interface from a user. In some embodiments the weight sensor 1504 does not include a user interface. The weighing surface 1540 is configured to provide a surface for a target container, such as an IV bag. The weighing surface 1540 can be sized so that an IV bag or other target container can be properly balanced and positioned on the weight sensor 1504 such that the weight sensor 1504 is configured to obtain an accurate measure of the weight of the IV bag or other target container. The weight sensor 1504 may provide information (e.g., weight measurements, current state of operation, etc.) to and receive commands from (e.g., zeroing the weight sensor) the fluid transfer station 1502 through a wired or wireless communication interface (not shown). As described in greater detail below, the weight sensor 1504 may be used to determine the amount of fluid transferred from the source container to the target container. These measurements can be used to calibrate the operation of the fluid transfer station 1502, to verify fluid transfer operations, and the like.

A foot pedal can be configured to provide user input to the system 1500 in addition to, or instead of, input provided through the user interface 1514. The foot pedal can allow the user to have both hands free (e.g., to replace IV bags after each fluid transfer of a multiple-IV bag order). In some embodiments, the foot pedal can issue a repeat command that causes the system 1500 to perform a fluid transfer of the same amount as the previous fluid transfer. In some embodiments, the foot pedal may provide an emergency stop command, such as when the foot pedal is activated during an active fluid transfer. The foot pedal can provide various other signals to the controller, such as an accept command, a pause command, a start command, a cancel command, etc.

In some embodiments, the system 1500 can include a printer that can be configured to automatically print labels for use with the fluid transfer station 1502 or other components. For example, when a fluid transfer is performed, the printer can print a label automatically to be placed on the target container (e.g., IV bag). The label can include information such as the fluid type, the concentration, the amount of fluid, the intended patient, the requesting doctor, etc. In some embodiments, the printer can be directly attached to the fluid transfer station 1502, such as by a wire or cable extending from a port on the fluid transfer station 1502. In some embodiments, the printer can communicate with the fluid transfer station 1502 by a wireless data connection. The controller of the fluid transfer station 1502 can be configured to generate the printer instructions for printing the labels. In some embodiments, some or all of the aspects of the printer may be incorporated into the fluid transfer station 1502 (e.g., located within a housing of the fluid transfer station 1502).

Figure 12:
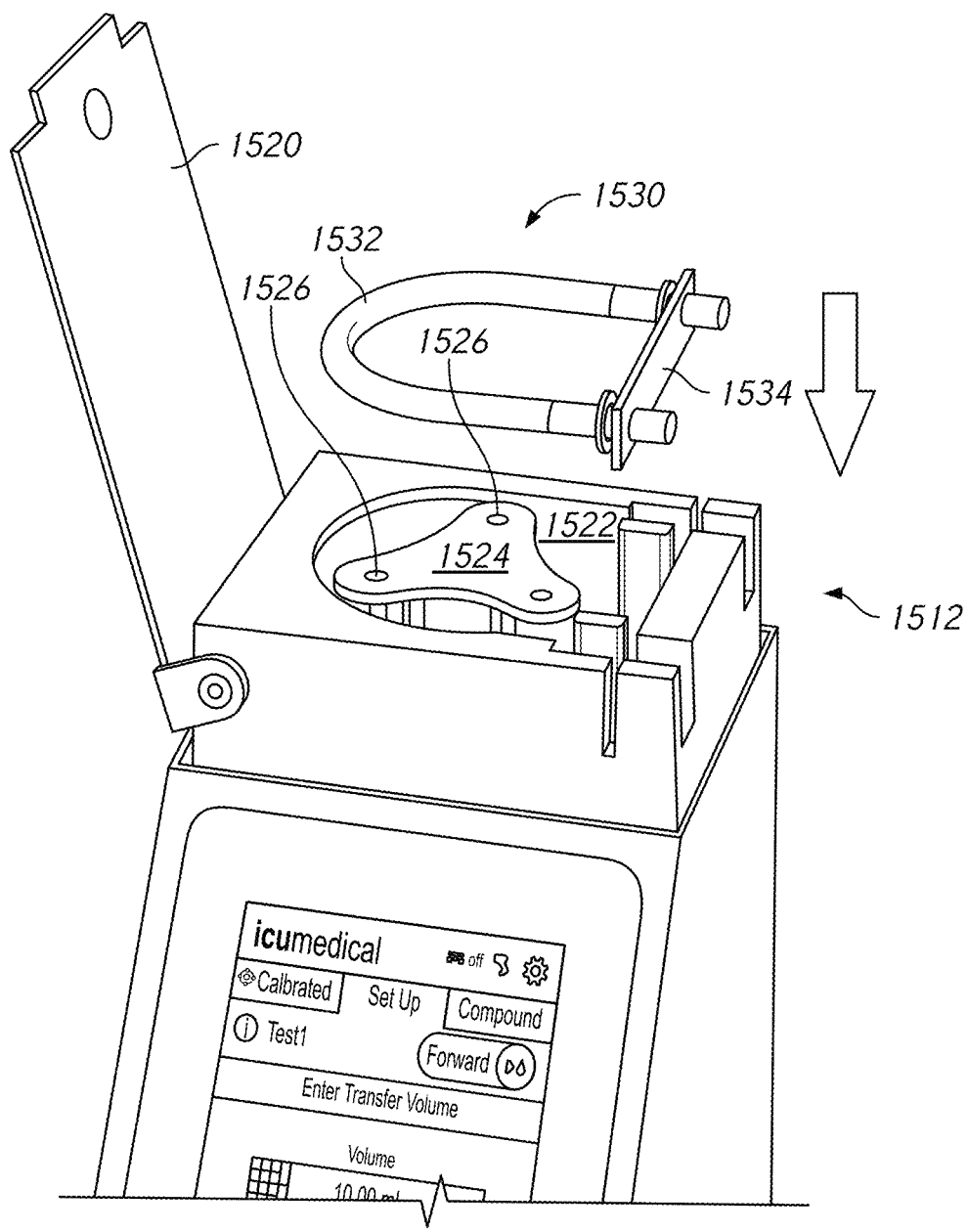
FIG. 12 is a top view of the system of FIG. 11 during installation of a fluidics assembly.

The fluid transfer station 1502 can be configured to transfer medical fluid from a source container (e.g., a vial, bag, or the like) to a target container (e.g., an IV bag) using the peristaltic pump 1512 and a fluidics assembly, such as the fluidics assembly 1530 shown in FIG. 12. The peristaltic pump 1512 is a positive displacement pump used for pumping fluid from a source container to a target container. The peristaltic pump 1512 may include a cover 1520 that shields components of the peristaltic pump 1512 and/or fluidics assembly 1530 during use, and prevents injury to users of the pump 1512. The peristaltic pump 1512 may also include a mounting interface 1522 configured to receive the fluidics assembly 1530. Fluid is transferred via a compressible tube 1532 of the fluidics assembly 1530 fitted inside the mounting interface 1522.

A rotor 1524 may be coupled to a motor of the peristaltic pump 1512, and the motor may cause the rotor 1524 to rotate around a central axis. One or more lobes 1526 may be attached to an external circumference of the rotor 1524 to compress the flexible tube 1532, which may be positioned substantially adjacent to the external circumference of the rotor 1524. In some embodiments the lobes 1526 can be rollers, shoes, wipers, or other members that facilitate the operation of the pump 1512. In some embodiments, the peristaltic pump 1512 may have the same number or a different number of lobes as the peristaltic pump 1350 described above. For example, while the peristaltic pump 1350 shown in FIG. 9 has four lobes 1356, the peristaltic pump 1512 shown in FIG. 12 has three lobes 1526. During operation, a plurality of lobes 1526 (e.g., at least two out of three lobes) may be in contact with the tube 1532 simultaneously, and the particular lobes 1526 that contact the tube 1532 vary over the course of operation as the rotor 1524 turns. As the rotor 1524 is turned by the motor of the peristaltic pump 1512, at least a portion of the tube 1532 is compressed, or occludes, thus forcing the fluid to move through the tangentially-oriented tube 1532 towards the target container. The tube 1532 may be resilient such that after the passing of the lobes 1526 over a portion of the tube 1532, the portion of the tube 1532 expands to its natural state and fluid flow is induced from the source container. This process of tube 1532 compression and expansion may be repeated for as long as the rotor 1524 rotates and the lobes 1526 contact and pass over the tube 1532. The volume of fluid transferred through the tube 1532 for each rotation (or fractional rotation) of the rotor 1524 may be determinable, as described in greater detail below, and may be used during operation of the peristaltic pump 1512 to accurately transfer a desired total volume of fluid to a target container.

The fluidics assembly 1530 may be similar to, or the same as, the fluidics assembly 1339 shown in FIGS. 5-6. In some embodiments, as shown in FIG. 12, the fluidics assembly 1530 may include a positioning member 1534 that is configured to fit within the mounting interface 1522 in a single or limited number of orientations, thereby ensuring proper installation for use of the fluidics assembly 1530. To install the fluidics assembly 1530, the cover 1520 is opened, the compressible tube 1532 and optional positioning member 1534 are positioned within the mounting interface 1522, and the cover 1520 is closed.

In some embodiments, as shown in FIGS. 11 and 12, the peristaltic pump 1512 is located on top of the housing 1510. In this configuration, the plane in which the rotor 1524 rotates is parallel (or substantially parallel) to the plane of the surface upon which the fluid transfer station 1502 is positioned, and is orthogonal (or substantially orthogonal) to the direction of gravity. Thus, gravity does not aid or impede the flow of fluid through the portion of the compressible tube 1532 that is installed into the mounting interface 1522, because the entire portion of the tube 1532 installed into the mounting interface 1522 is also positioned such that the path of fluid flow is substantially orthogonal to the direction of gravity at all points within the mounting interface 1522. Moreover, the source container and target container (not shown) may be positioned such that they are also coplanar with the rotor 1524, or are both above the plane of the rotor 1524, or are both below the plane of the rotor 1524. Therefore, any effect of gravity on one portion of the fluidics assembly 1530 are negated by the opposite effect of gravity on another portion of the fluidics assembly 1530. In contrast, if the plane in which the rotor 1524 rotates is parallel to (or is otherwise not orthogonal to) the direction of gravity, then gravity may aid or impede the flow of fluid at certain points within the compressible tube, which may cause inefficiencies and inconsistencies (e.g., due to backflow or free flow immediately before or after a lobe 1526 compresses and/or decompresses the tube).

FIG. 13 shows example internal components of the fluid transfer station 1502 to facilitate various features described herein. As shown, the fluid transfer station 1502 may include: one or more computer processors 1550, such as central processing units ("CPUs"); one or more communication interfaces 1552, such as a network interface cards ("NICs"), wireless communication antenna and related circuitry, etc.; one or more input/output device interfaces 1554; one or more motors 1556; one or more motor controller units ("MCUs") 1558 to control the operation of the motor(s) 1556; and one or more computer readable memories 1560, such as random access memory ("RAM") and/or other non-transitory computer-readable media. The computer readable memory 1560 may include data storage and/or computer program instructions that the computer processor(s) 1550 execute in order to implement one or more embodiments. For example, the computer readable memory 1560 can store an operating system 1562 that provides computer program instructions for use by the computer processor(s) 1550 in the general administration and operation of the fluid transfer station 1502. The computer readable memory 1560 may also include fluid transfer instructions 1564 for initiating and managing the transfer of fluid. The computer readable memory 1560 may also include an operational settings data store 1568 to store fluid transfer parameters and other operational settings of the fluid transfer station 1502. The computer readable memory 1560 may also include a drug library 1570—also referred to as a medication database—to store data regarding the medical fluids transferred via the fluid transfer station 1502.

Figure 14:
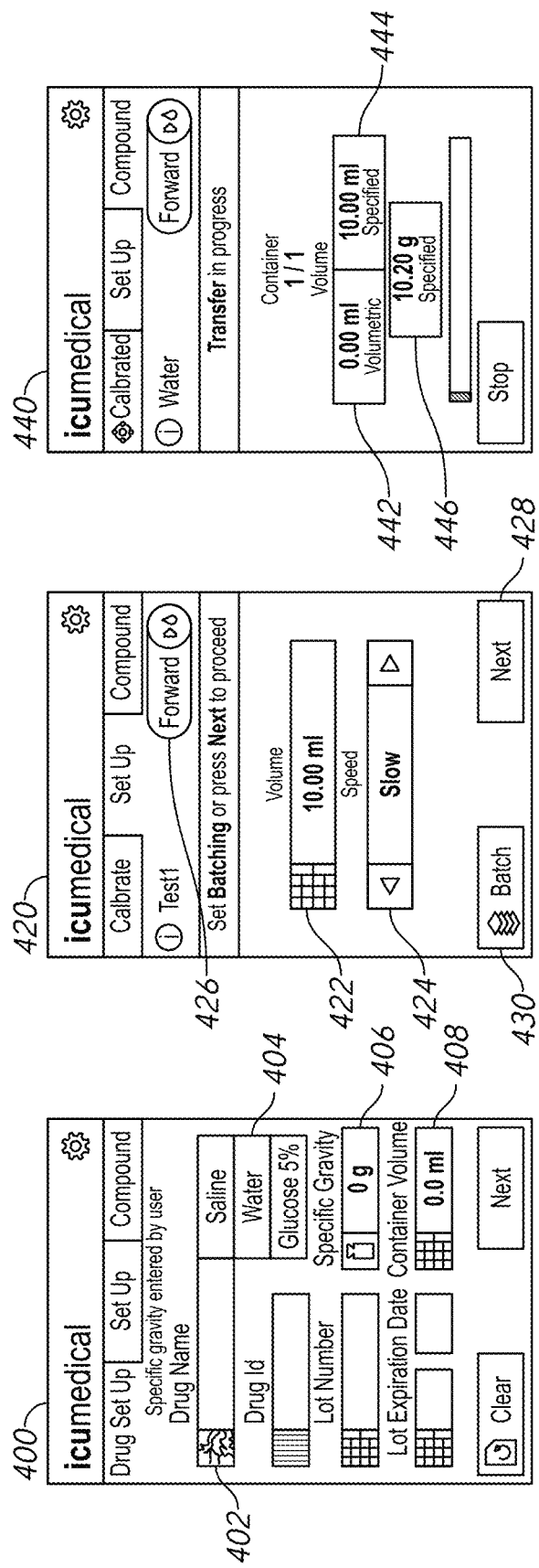
FIG. 14 is a view of user interfaces for managing the transfer of fluid using the system of FIG. 11.

FIG. 14 shows example user interface ("UI") displays 400, 420, and 440 for setting up and managing a fluid transfer operation using the fluid transfer system 1500. During a particular transfer operation, the peristaltic pump 1512 moves the fluid from the source container through the fluidics assembly 1530 and into the target container. An example of operation of an embodiment of a peristaltic pump is described in greater detail above with reference to FIG. 10. A user may initiate such a fluid transfer operation by selecting a medication via UI display 400. The user may enter or search for a medication profile using a medication entry control 402. In some embodiments, commonly-used or recently-used medication profiles may be available for faster selection using a quick select control 404. Upon selection of a medication profile, information may be loaded from a drug library and displayed on the UI display 400. For example, medication profile information may be loaded from the drug library 1570 of the fluid transfer station 1502 or obtained from another data store via a network, such as from a HIS. The UI display 400 may be updated to show aspects of the medication profile, such as the name of the fluid, an identifier, a lot number, an expiration, and the like.

In addition to—or instead of—such descriptive properties of the medication profile, the fluid transfer station 1502 may present fluid properties of the medication profile. For example, fluid properties may include the specific gravity 406 of the fluid (also referred to as the relative density), and the source container volume 408. As described in greater detail below, such fluid properties may affect the operation of the fluid transfer station 1502 in performing a fluid transfer operation, including the calibration of the fluid transfer station 1502 and/or verification of the fluid transfer operation. In some embodiments, the UI controls used to display the specific gravity 406, source container volume 408, or other fluid properties of the medication profile may allow editing of the displayed data. For example, a user may be permitted to modify the specific gravity of the fluid that is the subject of the displayed medication profile. Once a property has been edited, the UI display 400 may indicate that the property has been edited, such as by displaying an icon, changing a font characteristic, and/or preventing additional edits. In some embodiments, editing of medication profile data may be restricted to only authorized users (e.g., only authorized users may be permitted to change the specific gravities associated with medication profiles).

Once a medication profile has been selected (and optionally edited), the user may move to the next step of fluid transfer setup by selecting or providing transfer parameters. In some embodiments, UI display 420 may provide editable controls for setting transfer parameters. As shown, volume control 422 may allow selection or entry of a volume of fluid to be transferred from a source container to a target container. A speed control 424 may allow selection or entry of a speed at which the volume of fluid is to be transferred. The speed—or flow rate—at which fluid moves through the fluidics assembly 1530 can be controlled by the speed at which the MCU 1558 operates the motor 1556, which in turn controls the speed at which the rotor 1524 rotates. Users may wish to control the fluid flow rate based on one or more factors such as the viscosity of the fluid being transferred, the volume of fluid being transferred, and the like. A direction control 426 may allow selection or entry of a direction at which the fluid is to be transferred. For example, the options may be "forward" in which fluid is transferred from the source container to the target container, and "reverse" in which fluid is transferred back to the source container from the target container, or back to the source container from the fluidics system, which fills with air to replace the fluid. The "reverse" direction may be desirable when the fluid is expensive and preserving all unused fluid for future operations is preferable rather than to disposing of fluid along with a disposable fluidics assembly.

In some embodiments, the user may select a fluid transfer mode. For example, UI display 420 may include selectable controls for initiating a single transfer 428 (e.g., filling a single target container to a specified volume) or a batch transfer 430 (e.g., repeatedly transferring the desired volume of fluid to a configurable number of target containers). Batch transfer mode is described in greater detail below with respect to FIGS. 17 and 18.

Once a single fluid transfer operation has been initiated, UI display 440 may present the status of the transfer operation. For example, UI display 440 may include a transferred volume portion 442 that dynamically updates to display the volume of fluid that has been transferred from the start of the operation to the present time. UI display 440 may include a specified volume portion 444 that displays the total volume originally selected (e.g., via UI display 420) to be transferred to the target container.

UI display 440 may also include a specified weight portion 446 that displays the total weight of the fluid to be transferred to the target container. The fluid transfer station 1502 may determine the value to be displayed in the specified weight portion 446 based on one or more fluid properties and/or other aspects of the fluid transfer configuration. For example, the fluid transfer station 1502 may multiply the specific gravity—e.g., obtained from the selected medication profile or inputted by the user or sensed by a sensor—by the specified volume to be transferred to the target container in order to determine the specified weight according to the following equation:

$$w = sg \times v$$

where w=weight of the fluid in a given unit of weight (such as grams), sg=specific gravity of the fluid in the given unit of weight per a given unit of volume (such as grams per milliliter), and v=volume of the fluid in the given unit of volume (milliliters in this example).

The peristaltic pump 1512 may be configured to rotate the rotor 1524 a particular quantity of revolutions (or a particular fraction of a revolution) per volume unit of fluid to be transferred. For a transfer operation, the fluid transfer station 1502 may determine the quantity of revolutions that the rotor 1524 is to be rotated in order to cause transfer of the desired volume of fluid. The fluid transfer station 1502 may load an operation setting, such as a setting stored in the pump settings data store 1568, indicating the quantity of revolutions per unit of fluid to be transferred.

In some embodiments, multiple settings may be stored in the pump data store 1568, and individual settings may indicate a quantity of revolutions that the rotor 1524 is to be rotated per unit of fluid to be transferred, when the transfer operation is associated with different fluid properties and/or transfer parameters. For example, a first setting may be associated with fluid transfer operations occurring at a first speed (in terms of rotor revolutions per minute, units of fluid per minute, etc.), and a second setting may be associated with fluid transfer operations occurring at a second speed that is different than the first speed. As another example, a first setting may be associated with fluid transfer operations of fluids with a first specific gravity, while a second setting may be associated with fluid transfer operations of fluids with a second specific gravity that is different than the first specific gravity. As a further example, a first setting may be associated with fluid transfer operations of fluids with a first viscosity, while a second setting may be associated with fluid transfer operations of fluids with a second viscosity that is different than the first viscosity. In some embodiments, settings may be associated with combinations of fluid properties and/or fluid transfer parameters. For example, a first setting may be associated with fluid transfer operations of fluid with a first viscosity, where the transfer operations occur at a first speed, and so on.

The peristaltic pump 1512 may drift out of proper calibration for a number of reasons. For example, different fluidics assemblies may have subtle variances due to manufacturing tolerances that cause different volumes of fluid to be pumped through different assemblies for the same quantity of rotor rotations. As another example, as the motor is used its operational performance and specifications may gradually change due to wear. In some cases, environmental factors such as volume, humidity, altitude, barometric pressure, or the like may affect the calibration of the peristaltic pump 1512. To address these and other calibration issues, a calibration process may be performed on a periodic and/or on-demand basis.

Figure 15:
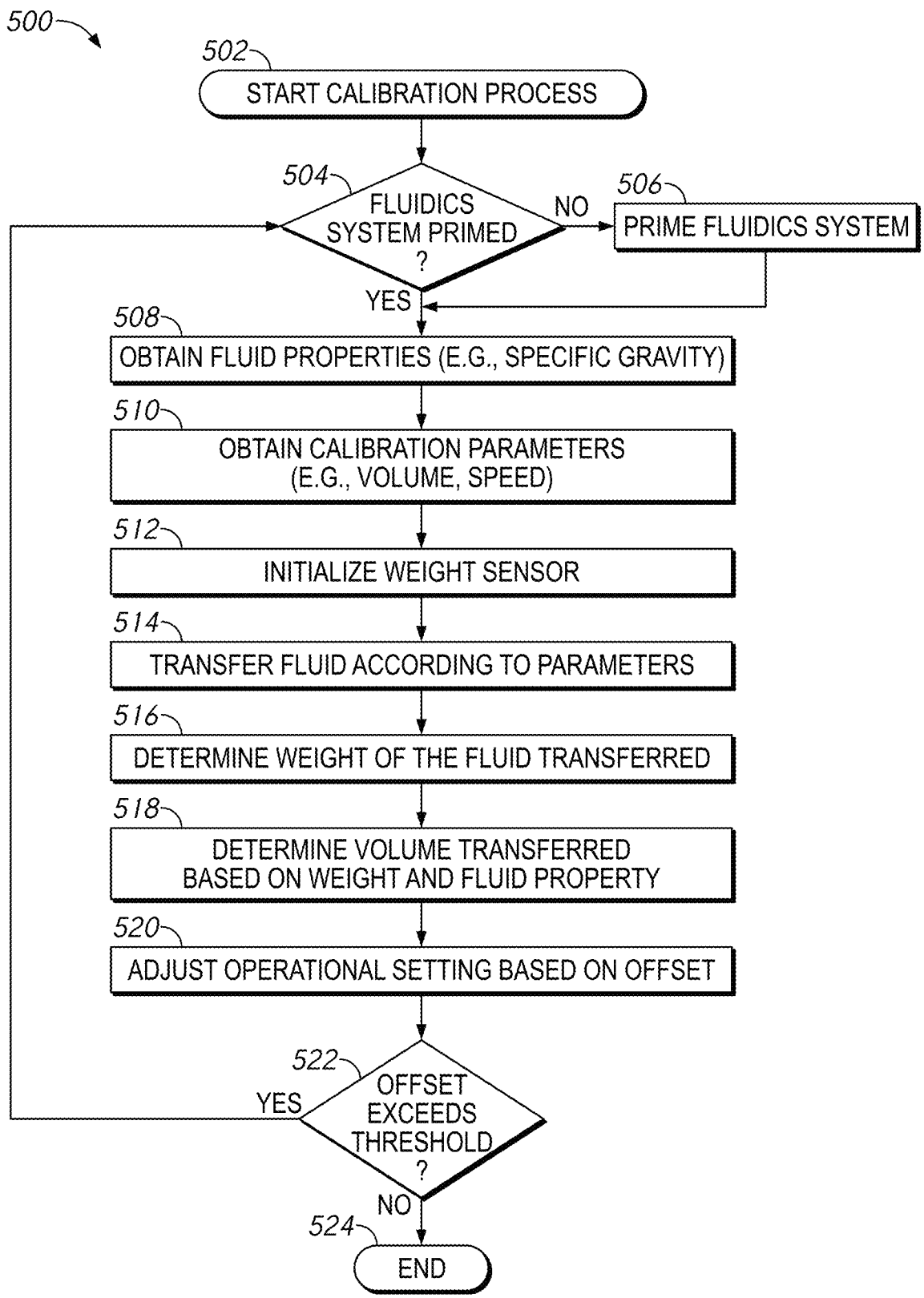
FIG. 15 is a flow diagram of an example embodiment of a method for calibrating an automated system for transferring fluid.
Figure 16:
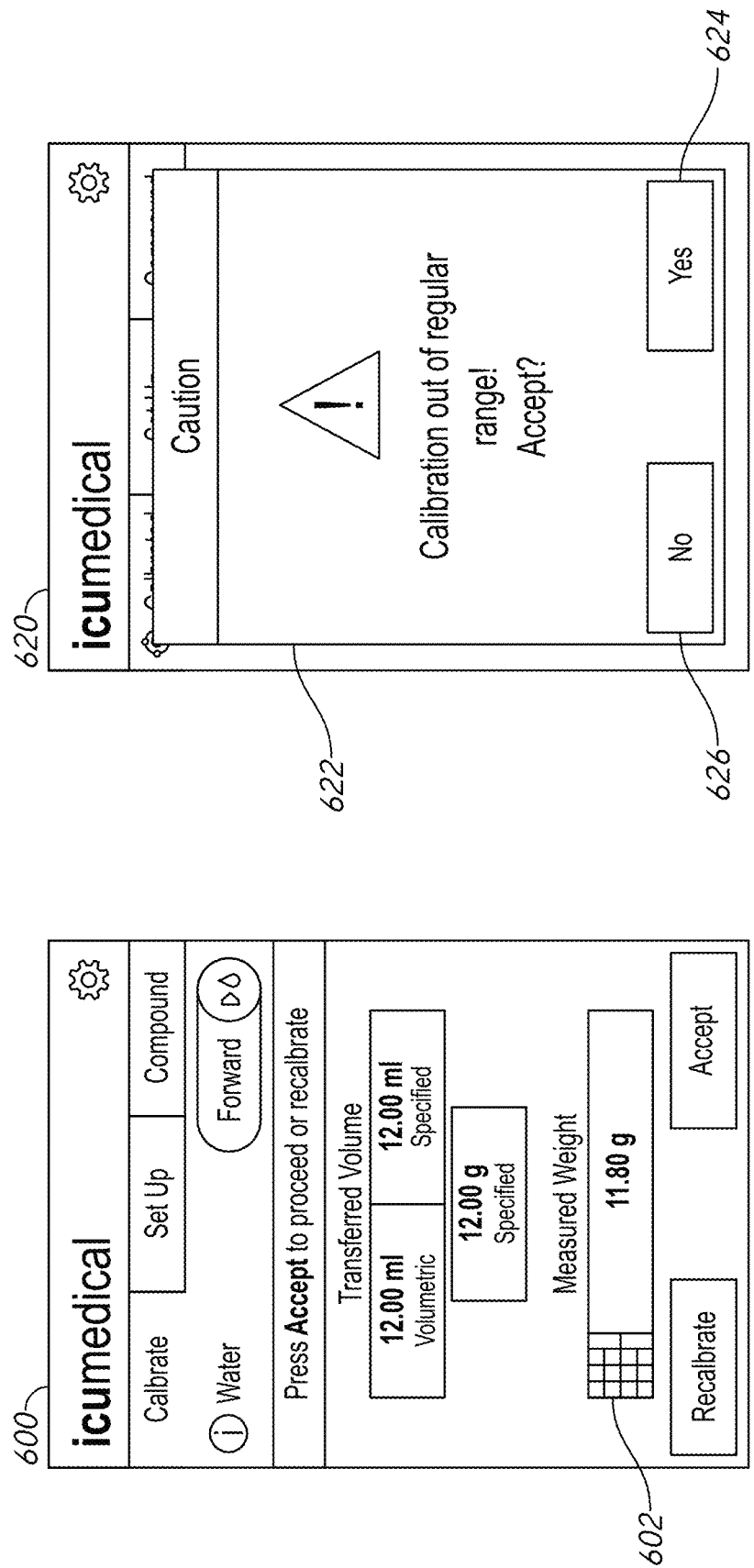
FIG. 16 is a view of user interfaces for managing the calibration of the system of FIG. 11.

FIG. 15 is a flowchart of an example process 500 that may be used to calibrate the fluid transfer station 1502 such that the volume of fluid transferred to a target container matches, or comes within a threshold amount or percentage of matching, the volume that was directed to be transferred. As described in greater detail below, the calibration process 500 involves transferring a desired volume of fluid using a current set of operational settings, measuring the volume that was actually transferred, determining an offset between the desired volume and the transferred volume, and adjusting the operational settings as needed so that future transfer operations result in the amount of volume transferred being the same as—or within an acceptable degree of accuracy of—the desired volume. Advantageously, in some embodiments the calibration process 500 can use the weight sensor 1504 and fluid properties in medication profiles to determine whether to modify operational settings—and if so, the degree to which the operational settings are to be modified—without requiring any specialized target container for the transferred fluid, and without requiring the transferred fluid to be removed from the target container for a volume measurement. Rather, the measurements during the calibration process 500 may be taken after transferring fluid to the same standard target containers used in routine transfer operations, including target containers from which the fluid will eventually be administered to patients. In this way, calibration may be performed more easily, and more often if needed, than alternative calibration methods.

The process 500 begins at block 502. The process may begin in response to an event, such as when the fluid transfer station 1502 is powered on, at recommended intervals, or on-demand. In some embodiments, calibration may be recommended or required periodically or in response to an event. For example, calibration may be recommended or required after each change of fluidics assembly, each change of desired volume, each change of target container type, or when the fluid transfer station 1502 has transferred a threshold volume of fluid since the last calibration (e.g., every 10,000, 30,000, or 100,000 milliliters of fluid transferred).

When the process 500 is initiated, a set of executable program instructions stored on one or more non-transitory computer-readable media (e.g., hard drive, flash memory, removable media, etc.) may be loaded into memory (e.g., random access memory or "RAM") of a computing device. For example, FIG. 13 shows an example fluid transfer station 1502 in which calibration instructions 1566 may be loaded into memory 1560, and executed by a processor 1550.

At decision block 504, the fluid transfer station 1502 can determine whether a fluidics assembly has been installed and primed. For example, the fluid transfer station 1502 may prompt a user via user interface 1514 to indicate whether the fluidics assembly is primed. If the fluidics assembly has not been primed, the process 500 may proceed to block 506 to prime the assembly. Otherwise, if the assembly has been primed, the process 500 may proceed to block 508.

At block 508, the fluid transfer station 1502 can obtain fluid properties for the fluid that is to be used during the calibration operation. In some embodiments, a user interface display with features that are similar to—or the same as—UI display 400 may be used to select the fluid that is to be used during the calibration operation. For example, determining fluid properties can include determining the specific gravity of the fluid to be transferred. The fluid transfer station 1502 may load the specific gravity from the drug library 1570 after selection of the particular fluid to be transferred. In some embodiments, other fluid properties may be determined, such as the viscosity of the fluid to be transferred.

At block 510, the fluid transfer station 1502 can obtain transfer parameters for the calibration operation. In some embodiments, a user interface display with features that are similar to—or the same as—UI display 420 may be used to select the volume of fluid that is to be transferred during the calibration operation. In some embodiments, other fluid transfer parameters properties may be determined, such as the speed at which fluid is to be transferred. The fluid transfer station 1502 may also obtain the current operational settings in order to manage the transfer of fluid. For example, the fluid transfer station 1502 may load a setting, stored in the pump settings data store 1568, indicating the quantity of revolutions per unit of fluid to be transferred. The operational setting may be a universal setting that applies to all fluids and transfer operations, or it may be an operational setting that applies to transfer of fluids with specific fluid properties (e.g., viscosity, specific gravity, etc.) and/or using specific transfer parameters (e.g., speed, type of fluidics assembly, etc.).

At block 512, the weight sensor 1504 can be initialized. Initialization of the weight sensor 1504 may be performed to ensure that weight measurements generated by the weight sensor 1504 are accurate. In some embodiments, the weight sensor may be initialized to account for tare. For example, the weight sensor 1504 may be initialized such that it produces a weight measure of 0.0 units when an empty target container is on the weight sensor 1504. Accordingly, when fluid is transferred into the target container, the weight sensor 1504 will indicate the weight of the fluid only, and not the target container.

At block 514, the fluid transfer station 1502 can initiate transfer of the indicated volume of fluid to the target container. Transfer of the volume of fluid may proceed in a manner similar to—or the same as—transfer of fluid in a non-calibration-related transfer operation as described in greater detail above. In some embodiments, a user interface display with features that are similar to—or the same as—UI display 440 may be used to present the status of the fluid transfer operation.

At block 516, a measurement of the transferred volume of fluid can be determined. The measurement may be a weight measurement of the transferred fluid, as measured by the weight sensor 1504. The measurement may be provided from the weight sensor 1504 to the fluid transfer station 1502 via wired or wireless transmission. For example, after the fluid transfer station 1502 completes transfer of the volume of fluid using the operational settings, the fluid transfer station 1502 may request, read, receive, or otherwise obtain a measurement from the weight sensor 1504. In some embodiments, rather than obtaining the weight via transmission from the weight sensor 1504, the weight may be provided to the fluid transfer station 1502 by a user via a user interface. For example, UI display 600 shown in FIG. 6 may provide an interactive control 602 for entering, selecting, or otherwise providing a weight measurement. The user may review a user interface of the weight sensor 1504 to determine the weight measured by the weight sensor 1504, and then provide the determined weight measurement to the fluid transfer station 1502 via the UI display 600.

At block 518, the fluid transfer station 1502 can determine an observed volume of fluid transferred to the target container based on the weight measurement obtained in block 516 above, and a property of the fluid such as the specific gravity of the fluid. For example, the fluid transfer station 1502 may divide the measured weight of the transferred fluid by the specific gravity from the selected medication profile to arrive at the observed volume transferred to the target container, according to the following equation:

$$v = w/sg$$

where w=weight of the fluid in a given unit of weight (such as grams), sg=specific gravity of the fluid in the given unit of weight per a given unit of volume (such as grams per milliliter), and v=volume of the fluid in the given unit of volume (such as milliliters).

At block 520, the fluid transfer station 1502 can determine an adjustment to address any difference between the observed volume and the desired volume. The fluid transfer station 1502 may first analyze the observed volume with respect to the desired volume to determine whether there is a difference or "offset." If there is an offset, the fluid transfer station 1502 may adjust an operational setting to address the offset. For example, the fluid transfer station 1502 may determine that the number of rotor revolutions previously used to transfer the desired volume is now associated with the observed volume, which is different than the desired volume. A modification to the operational setting that represents the number of rotor revolutions may be made to ensure that use of the operational setting produces the desired volume. In some embodiments, adjusting the setting may be based on the magnitude and direction of the offset. For example, the offset may be based on the percentage of the observed volume in terms of the desired volume: a positive value indicates greater than 100% of the desired volume has been transferred, and a negative value indicates less than 100% of the desired volume has been transferred. The operational setting may be adjusted by the offset value: reducing the setting by a percentage corresponding to the offset value if the sign of the offset is positive (indicating an overfill), and increasing the setting by a percentage corresponding to the offset value if the sign of the offset is negative (indicating an underfill).

At decision block 522, the fluid transfer station 1502 can determine whether the offset determined above at block 520 is within a calibration threshold. An offset exceeding a calibration threshold may indicate that a relatively large change to the operational setting was made. A large offset may have been anomalous, or a large change to the operational setting may be associated with less than desired precision. In such cases, the calibration process 500 may return to block 504 and be performed again to verify that the change made to the operational setting indeed results in the desired volume of fluid being transferred. The re-performance of the calibration process may be automatic or required. For example, in response to determining that the offset is outside of the calibration threshold, use of the fluid transfer station 1502 may not be permitted until the calibration process 500 is performed again. In some embodiments, re-performance of the calibration process 500 may be optional or manually initiated. For example, a user interface such as UI display 620 shown in FIG. 6 may provide a warning or other indication 622 that the offset exceeds a calibration threshold. A user may accept the calibration change (e.g., by activating an acceptance control 624), or choose to perform another calibration process (e.g., by activating a re-calibration control 626) to verify that the change has brought the fluid transfer station 1502 within the desired level of calibration.

At block 524, the process 500 may terminate.

In addition to being performed on-demand or in response to particular recommendations, calibration may be incorporated into a batch process at regular intervals. In some embodiments, a user may configure the fluid transfer station 1502 to transfer a same volume of fluid to a predetermined number of target containers without requiring reconfiguration of the fluid transfer station 1502 between target containers. For example, a same volume of saline (e.g., 100 ml) may be transferred from a large source container to multiple individual target containers (e.g., 5, 10, 50, or more individual target containers) after a single setup operation, without requiring a corresponding number of setup operations (e.g., without requiring 5, 10, 50, or more setup operations using the UI displays 400, 420, 440). In order to detect and address any calibration issues that may arise during the batch operation, periodic calibration checks may be performed during the batch process.

Figure 17:
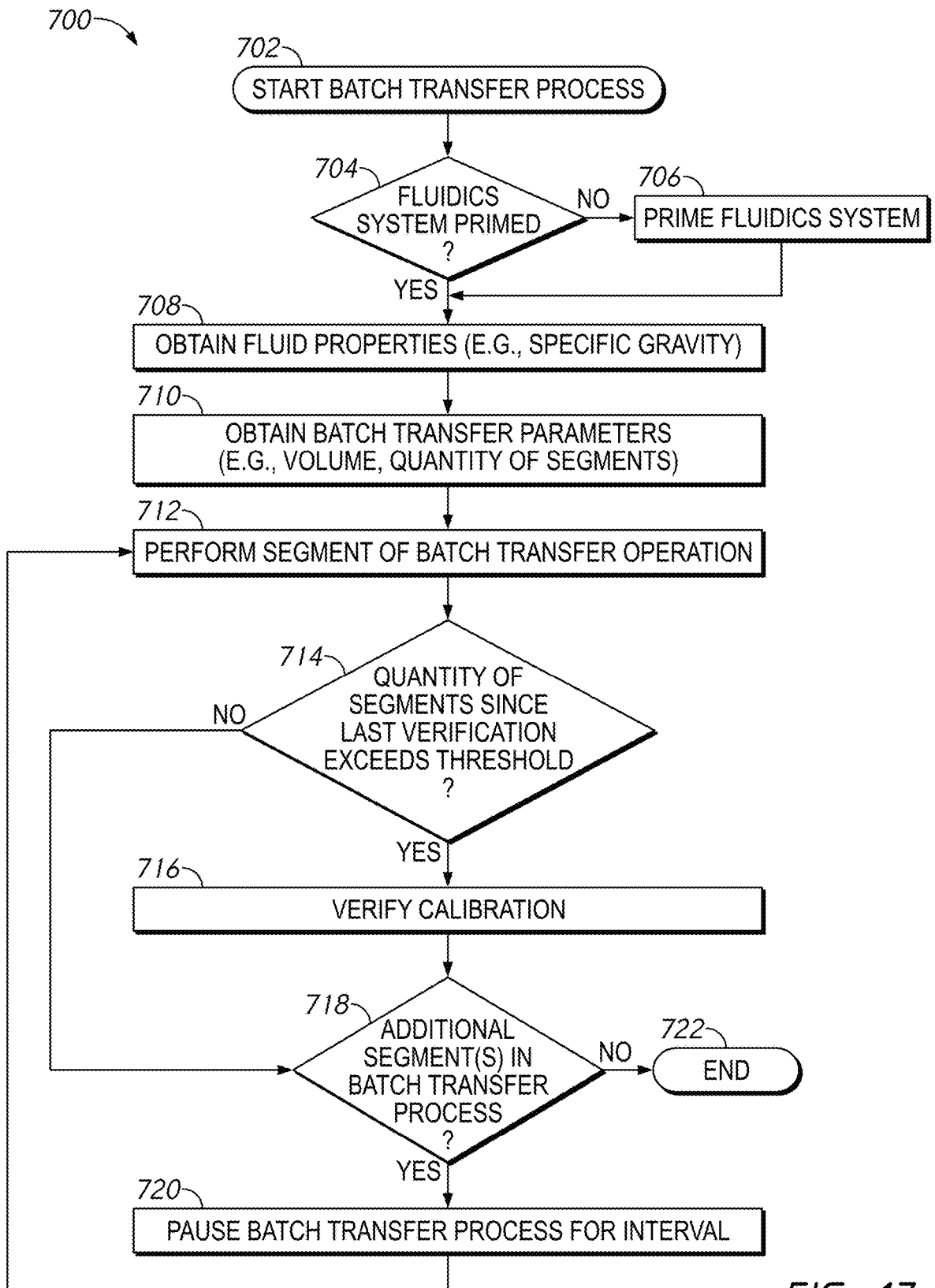
FIG. 17 is a flow diagram of an example embodiment of batch fluid transfer method with periodic verification.

FIG. 17 is a flowchart of an example process 700 that may be used to perform a batch transfer of fluid to multiple target containers while periodically checking the calibration of the fluid transfer station 1502. As described in greater detail below, the batch transfer process 700 involves iteratively transferring a desired volume of fluid using a current set of operational settings, periodically measuring the volume that was actually transferred, and adjusting the operational settings as needed. Advantageously, the batch transfer process 700 uses the weight sensor 1504 and fluid properties in medication profiles to verify the calibration of the fluid transfer station 1502.

The process 700 begins at block 702. The process may begin in response to an event, such as when a user accesses a user interface to initiate a batch transfer process. When the process 700 is initiated, a set of executable program instructions stored on one or more non-transitory computer-readable media (e.g., hard drive, flash memory, removable media, etc.) may be loaded into memory (e.g., random access memory or "RAM") of a computing device. For example, FIG. 13 shows an example fluid transfer station 1502 in which fluid transfer instructions 1564 may be loaded into memory 1560, and executed by a processor 1550.

At block decision block 704, the fluid transfer station 1502 can determine whether a fluidics assembly has been installed and primed. For example, the fluid transfer station 1502 may prompt a user via user interface 1514 to indicate whether the fluidics assembly is primed. If the fluidics assembly has not been primed, the process 700 may proceed to block 706 to prime the assembly. Otherwise, if the assembly has been primed, the process 700 may proceed to block 708.

At block 708, the fluid transfer station 1502 can obtain fluid properties for the fluid that is to be used during the batch transfer operation. In some embodiments, a user interface display with features that are similar to—or the same as—UI display 400 may be used to select the fluid that is to be used during the batch transfer operation. For example, determining fluid properties can include determining the specific gravity of the fluid to be transferred. The fluid transfer station 1502 may load the specific gravity from the drug library 1570 after selection of the particular fluid to be transferred. In some embodiments, other fluid properties may be determined, such as the viscosity of the fluid to be transferred.

At block 710, the fluid transfer station 1502 can obtain transfer parameters for the batch transfer operation. In some embodiments, a user interface display with features that are similar to—or the same as—UI display 420 may be used to select the volume to be transferred in each segment of the batch transfer operation, and the speed at which the desired volume is to be transferred in each segment. In addition to these transfer parameters, additional parameters may be set for the batch transfer operation. A user interface display, such as UI display 800 in FIG. 18, may be presented to facilitate the configuration of additional parameters of batch transfer operation. For example, the UI display 800 may include an interactive segment entry control 802 for selecting or entering a desired quantity of target containers into which the desired volume of fluid is to be transferred. The batch transfer operation will include a segment for each target container. The UI display 800 may also include an interactive interval time control 804 for selecting or entering the desired length of time to be used as the interval between each segment of the batch transfer operation. The interval provides time for the user of the fluid transfer station 1502 to perform various tasks related to completion of a segment and/or preparation for a next segment, such as disconnecting a target container—filled during the most-recently-completed segment of the batch transfer operation—from the fluidics system, connecting a new empty target container to the fluidics system for the next segment of the batch transfer operation, etc.

At block 712, a segment of the batch transfer process may be performed. The fluid transfer performed in each individual segment of the batch transfer process may proceed in a manner similar to—or the same as—transfer of fluid in a non-batch transfer operation as described in greater detail above. In some embodiments, a user interface display such as UI display 820 may be used to present the status and results of the current segment. UI display 820 may include a segment indicator portion 822 to indicate which segment of the batch transfer operation is currently in progress, a transferred volume portion 824 to indicate the volume transferred the far during the current segment of the batch transfer process, a desired volume portion 826 to indicate the desired volume to be transferred during the current segment, and an interval indicator portion 828 to indicate the length of the interval between segments (e.g. a quantity of units of time, such as seconds).

At decision block 714, after the current segment of the batch transfer process has completed, the fluid transfer station 1502 can determine whether a number of segments transferred since the last calibration check—or since the beginning of the process 700—has reached a verification threshold. If so, the process proceeds to block 716 to verify the calibration based on the most recently completed segment of the batch transfer process. Otherwise, the process may continue at decision block 718. The verification threshold may be a predetermined value, such as an operational setting of the fluid transfer station 1502. For example, the threshold may be set to a value (e.g., 10, 50, 100) when the fluid transfer station 1502 is manufactured, maintained by an administrator, or the like. In some embodiments, the verification threshold may be configurable for a given batch transfer process. For example, a UI display such as UI display 800 may include an interactive control for selecting or entering the verification threshold to be used for the current batch transfer process, At block 716, the calibration of the fluid transfer station 1502 can be verified based on the most recently completed segment of the fluid transfer process. The calibration may be verified based on the weight of the filled target container. In some embodiments, a process that is the same—or similar to—the calibration process 500 described in greater detail above may be used. For example, a user may place the filled target container on the weight sensor 1504. The weight measured by the weight sensor 1504 may be provided to the fluid transfer station 1502 automatically (e.g., via wired or wireless communication between the weight sensor 1504 and the fluid transfer station 1502), or manually (e.g., the user may enter the weight measurement in a user interface of the fluid transfer station 1502). The fluid transfer station 1502 may determine the observed volume of fluid transferred to the target container based on the weight using a fluid property, such as the specific gravity of the fluid, as described in greater detail above. The fluid transfer station may further determine an offset between the observed volume of fluid and the desired volume fluid, as also described in greater detail above. An operational setting may be automatically changed based on the offset, or the user may be prompted as to whether to update the operational setting.

At decision block 718, the fluid transfer station 1502 can determine whether there are any additional segments of the batch transfer process to be completed. If so, the process 700 can proceed to block 720. Otherwise, the process may terminate at block 722.

At block 720, there are one or more additional segments of the batch transfer process to be completed, and the fluid transfer station 1502 can wait for the designated interval between segments before returning to block 712 for the next segment. The interval provides time for the user of the fluid transfer station 1502 to perform various tasks related to completion of a segment and/or preparation for a next segment, such as disconnecting a target container—filled during the most-recently-completed segment of the batch transfer operation—from the fluidics system, connecting a new empty target container to the fluidics system for the next segment of the batch transfer operation, etc. In some embodiments, a UI display (such as UI display 820) may include a dynamic interval time indicator (not shown) that indicates the amount of time remaining in the interval before the next segment of the batch transfer process is to begin. If the user requires additional time between segments or otherwise wishes to pause or stop the batch transfer process, the user may activate a control on a UI display, activate the pedal, or use other input method.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as programmable computer central processing unit (CPU), a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. When a method, process, routine, or algorithm is to be executed, executable instructions may be loaded to or accessed at a storage medium and executed by one or more processors. In some embodiments, the storage medium can be integral to the processor device. The processor device and the storage medium can reside in an ASIC. The ASIC can reside in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

The following is claimed:

1. A medical fluid transfer system comprising:
   a pump comprising a rotor with one or more lobes, wherein the pump is configured to transfer fluid through a tube assembly having a first connector configured to couple to a source container and a second connector configured to couple to a target container;
   a destination sensor configured to output information about the target container; and
   a control system configured to:
   receive an instruction to transfer a desired volume of a medical fluid to the target container;
   operate the pump based on the instruction and an operational setting associated with a first quantity of rotations that the rotor is to be rotated for transfer of a fluid volume of the medical fluid;
   receive measurement data representing a measurement of the target container by the destination sensor;
   determine a difference between a transferred volume of the medical fluid and the desired volume of the medical fluid based at least partly on the measurement data and a fluid property of the medical fluid;
   adjust the operational setting based on the difference to a second quantity of rotations that the rotor is to be rotated for transfer of the fluid volume of the medical fluid; and
   operate the pump based on the operational setting that has been adjusted.

2. The medical fluid transfer system of claim 1, further comprising the tube assembly.

3. The medical fluid transfer system of claim 1, wherein the destination sensor comprises a weight sensor, and wherein the measurement data represents a weight of the target container after operation of the pump.

4. The medical fluid transfer system of claim 1, wherein the control system comprises a user interface, and wherein the measurement data is received by the control system via the user interface.

5. The medical fluid transfer system of claim 1, wherein the control system comprises a first communication interface, wherein the destination sensor comprises a second communication interface, wherein the destination sensor transmits the measurement data via the second communication interface, and wherein the measurement data is received by the control system via the first communication interface.

6. The medical fluid transfer system of claim 1, wherein the fluid property comprises a specific gravity of the medical fluid, and wherein the control system is further configured to determine the transferred volume of medical fluid based on the specific gravity and a weight of the target container represented by the measurement data.

7. The medical fluid transfer system of claim 1, wherein the control system is further configured to determine an adjustment to the operational setting based on a magnitude of the difference.

8. The medical fluid transfer system of claim 1, wherein the pump is a peristaltic pump.

9. The medical fluid transfer system of claim 8, further comprising a housing, wherein the housing is configured to support the peristaltic pump in a position in which a plane of rotation of the rotor is substantially orthogonal to a direction of gravity during operation of the peristaltic pump.

10. The medical fluid transfer system of claim 8, wherein the peristaltic pump is configured to operate at a plurality of speed settings.

11. The medical fluid transfer system of claim 1, wherein the control system is further configured to manage a batch transfer operation in which the control system operates the pump to transfer the desired volume of the medical fluid to each of a plurality of target containers.

12. The medical fluid transfer system of claim 11, wherein the control system is further configured to delay a subsequent segment of the batch transfer operation for a predetermined time interval after completion of a prior segment of the batch transfer operation.

13. The medical fluid transfer system of claim 11, wherein the control system is further configured to determine that the medical fluid has been transferred to a threshold quantity of target containers during the batch transfer operation, wherein the measurement data is received in response to the control system determining that the medical fluid has been transferred to the threshold quantity of target containers.

14. A method for calibrating a medical fluid transfer system, the method comprising:
 under control of a control system of the medical fluid transfer system, the control system comprising one or more computer processors configured to execute specific instructions:
  receiving an instruction to transfer a desired volume of a medical fluid to a target container;
  operating a pump of the medical fluid transfer system based on the instruction and an operational setting, wherein the pump comprises a rotor and one or more lobes, and wherein the operational setting is associated with a first quantity of rotations that the rotor is to be rotated for transfer of a fluid volume of the medical fluid;
  receiving measurement data representing a measurement of the target container by a destination sensor;
  determining a difference between a transferred volume of the medical fluid and the desired volume of the medical fluid based at least partly on the measurement data and a fluid property of the medical fluid; and
  adjusting the operational setting based on the difference to a second quantity of rotations that the rotor is to be rotated for transfer of the fluid volume of the medical fluid.

15. The method of claim 14, further comprising operating the pump using the operational setting that has been adjusted.

16. The method of claim 14, further comprising determining the transferred volume of the medical fluid based on the fluid property and the measurement data, wherein the fluid property comprises a specific gravity of the medical fluid, and wherein the measurement data represents a weight of the target container.

17. The method of claim 14, further comprising determining an adjustment to the operational setting based on a magnitude of the difference.

18. The method of claim 14, further comprising loading the operational setting from a data store, wherein the operational setting indicates a quantity of rotations that a rotor of the pump is to be rotated for transfer of one or more volumetric units of the medical fluid.

19. The method of claim 14, further comprising:
 managing a batch transfer operation in which the desired volume of the medical fluid is transferred to each of a plurality of target containers; and
 delaying a segment of the batch transfer operation for a predetermined time interval after completion of a prior segment of the batch transfer operation.

* * * * *